(12) United States Patent
Kim et al.

(10) Patent No.: US 10,993,910 B2
(45) Date of Patent: May 4, 2021

(54) BIOPATCH, BIOHEATER, BIOSENSOR AND BIOELECTRONIC PATCH DEVICE

(71) Applicants: SEOUL NATIONAL UNIVERSITY R&DB FOUNDATION, Seoul (KR); INSTITUTE FOR BASIC SCIENCE, Daejeon (KR)

(72) Inventors: Daehyeong Kim, Incheon (KR); Seunghong Choi, Seoul (KR); Taeghwan Hyeon, Seoul (KR); Jongha Lee, Seoul (KR); Hyerim Cho, Seoul (KR); Hyunseon Seo, Incheon (KR)

(73) Assignees: SEOUL NATIONAL UNIVERSITY R&DB FOUNDATION; INSTITUTE FOR BASIC SCIENCE

( * ) Notice: Subject to any disclaimer, the term of this patent is extended or adjusted under 35 U.S.C. 154(b) by 32 days.

(21) Appl. No.: 16/467,943

(22) PCT Filed: Dec. 7, 2016

(86) PCT No.: PCT/KR2016/014330
§ 371 (c)(1),
(2) Date: Jun. 7, 2019

(87) PCT Pub. No.: WO2018/105779
PCT Pub. Date: Jun. 14, 2018

(65) Prior Publication Data
US 2020/0030236 A1 Jan. 30, 2020

(51) Int. Cl.
*A61K 9/00* (2006.01)
*A61K 9/70* (2006.01)
(Continued)

(52) U.S. Cl.
CPC .......... *A61K 9/0085* (2013.01); *A61K 9/7007* (2013.01); *A61K 47/02* (2013.01); *A61K 47/34* (2013.01); *A61K 47/36* (2013.01)

(58) Field of Classification Search
CPC ................ A61K 9/0085; A61K 9/7007; A61F 2007/0071; A61F 7/007; G01N 27/327
See application file for complete search history.

(56) References Cited

U.S. PATENT DOCUMENTS

2003/0175328 A1* 9/2003 Shefer ..................... A61Q 19/02
424/449
2011/0245824 A1 10/2011 Schaffer
(Continued)

FOREIGN PATENT DOCUMENTS

EP        0153200 A2 *  8/1985  .............. A61K 47/44
JP     2010531343 A      9/2010
(Continued)

OTHER PUBLICATIONS

FAOWHO (http://www.fao.org/3/a-bq694e.pdf) 2016, pp. 1-3 (Year: 2016).*

*Primary Examiner* — Andrew S Rosenthal
(74) *Attorney, Agent, or Firm* — Renaissance IP Law Group LLP

(57) ABSTRACT

A biopatch, a bioheater, a biosensor and a bioelectronic patch device are provided.

The biopatch comprises a polymer film comprising a biopolymer and a drug loaded in the polymer film. The biopolymer may comprise one or more than one of a bioabsorbable polymer, a biodegradable polymer and a biocompatible polymer. The biopolymer may comprise oxidized starch. The drug may comprise a first drug chemically combined with the oxidized starch and a second drug physically combined with the oxidized starch.

The bioheater comprises a heater comprising biometal. The biometal may comprise Mg or Fe. The heater can be controlled wirelessly by an alternating magnetic field.

A biosensor according to one embodiment of the present inventive concept comprises an inductor and a capacitor connected to the inductor, wherein the capacitor comprises a first electrode, a second electrode facing the first electrode and a dielectric disposed between the first electrode and the second electrode, each of the inductor, the first electrode and the second electrode comprises biometal, and the dielectric comprises a biopolymer having a glass transition temperature in a range of 36~42° C. A biosensor according to another embodiment of the present inventive concept comprises an inductor and a capacitor connected to the inductor, wherein the capacitor comprises a first electrode, a second electrode facing the first electrode and a dielectric disposed between the first electrode and the second electrode, a change in a dielectric constant of the dielectric is transmitted to an external device through a resonance frequency change with the inductor, and the external device measures temperature around the biosensor by measuring the resonance frequency change wirelessly.

A bioelectronic patch device according to one embodiment of the present inventive concept comprises a drug patch comprising a polymer film comprising a biopolymer and a drug loaded in the polymer film, and a heater adjacent to the drug patch to heat the drug patch. A bioelectronic patch device according to another embodiment of the present inventive concept comprises a drug patch comprising a polymer film comprising a biopolymer and a drug loaded in the polymer film, a first protection layer disposed on the drug patch, a heater disposed on the first protection layer and heating the drug patch, a temperature sensor disposed on the first protection layer, spaced apart from the heater and measuring temperature of the heater, and a second protection layer covering the heater and the temperature sensor on the first protection layer.

13 Claims, 22 Drawing Sheets

(51) Int. Cl.
    *A61K 47/02*    (2006.01)
    *A61K 47/34*    (2017.01)
    *A61K 47/36*    (2006.01)

(56) References Cited

U.S. PATENT DOCUMENTS

2013/0140649 A1    6/2013    Rogers et al.
2016/0082124 A1    3/2016    Venkatesh et al.

FOREIGN PATENT DOCUMENTS

KR    20100117602 A    11/2010
WO    2010084088 A2    7/2010

\* cited by examiner (a)

(b)

(a)

(b)

(a)

(b)

BIOPATCH, BIOHEATER, BIOSENSOR AND BIOELECTRONIC PATCH DEVICE

TECHNICAL FIELD

The present disclosure relates to a biopatch, a bioheater, a biosensor and a bioelectronic patch device.

BACKGROUND ART

Surgical techniques and a variety of treatments such as radiation therapy, chemotherapy and the like have been developed in relation to brain tumors. However, malignant brain tumor cells may invade normal brain tissue to cause brain tumor recurrence even after brain tumor removal surgery. Therefore, it is necessary to remove brain tumor cells remaining at the surgical site after brain tumor removal surgery. However, it is difficult to inhibit or remove brain tumor cells remaining after surgery using treatments such as radiotherapy or chemotherapy that are currently used.

DISCLOSURE

Technical Problem

In order to solve the above mentioned problems, the present disclosure provides a biopatch that can be disposed and used in a living body such as a human body.

The present disclosure provides a biopatch that can deliver a drug effectively.

The present disclosure provides a bioheater that can be disposed and used in a living body such as a human body.

The present disclosure provides a bioheater that is controlled wirelessly.

The present disclosure provides a biosensor that can be disposed and used in a living body such as a human body.

The present disclosure provides a biosensor that is controlled wirelessly.

The present disclosure provides a bioelectronic patch device that can be disposed and used in a living body such as a human body.

The present disclosure provides a bioelectronic patch device that can deliver a drug effectively.

The other objects of the present disclosure will be clearly understood with reference to the following detailed description and the accompanying drawings.

Technical Solution

A biopatch according to embodiments of the present inventive concept comprises a polymer film comprising a biopolymer and a drug loaded in the polymer film.

The biopolymer may comprise one or more than one of a bioabsorbable polymer, a biodegradable polymer and a biocompatible polymer. The biopolymer may comprise oxidized starch.

The drug may comprise a first drug chemically combined with the oxidized starch and a second drug physically combined with the oxidized starch. An amount of the first drug can be controlled by controlling an oxidation concentration of the oxidized starch.

The biopatch may further comprise a heater adjacent to the polymer film to heat the polymer film. The heater may comprise biometal. The biometal may comprise Mg or Fe. The heater may comprise a metal pattern formed of the biometal. The metal pattern may have a plurality of holes. The heater can be controlled wirelessly by an alternating magnetic field. Release of the drug can be controlled by the heater.

The biopatch may further comprise a temperature sensor adjacent to the heater to measure temperature of the heater. The temperature sensor may comprise an inductor and a capacitor connected to the inductor, and the capacitor may comprise a first electrode, a second electrode facing the first electrode and a dielectric disposed between the first electrode and the second electrode. Each of the inductor, the first electrode and the second electrode may comprise biometal, and the dielectric may comprise a biopolymer having a glass transition temperature in a range of 36~42° C. The biometal may comprise Mg or Fe, and the biopolymer may comprise PLGA. A dielectric constant of the dielectric changes by a temperature change of the heater, the change in the dielectric constant is transmitted to an external device through a resonance frequency change with the inductor, and the external device can measure temperature of the heater by measuring the resonance frequency change wirelessly.

The biopatch can be inserted into brain tissue to be used for treatment of a brain tumor.

A bioheater according to embodiments of the present inventive concept comprises a heater comprising biometal.

The biometal may comprise Mg or Fe.

The heater may comprise a metal pattern formed of the biometal. The metal pattern may have a plurality of holes.

The bioheater may further comprise a first heater protection layer disposed below the heater and a second heater protection layer disposed on the heater.

The heater can be controlled wirelessly by an alternating magnetic field.

The heater may be adjacent to a biopatch to heat the biopatch. The biopatch may comprise a polymer film comprising a biopolymer and a drug loaded in the polymer film.

Release of the drug can be controlled by the heater.

The bioheater can be inserted into brain tissue together with the biopatch to be used for treatment of a brain tumor.

A biosensor according to one embodiment of the present inventive concept comprises an inductor and a capacitor connected to the inductor, wherein the capacitor comprises a first electrode, a second electrode facing the first electrode and a dielectric disposed between the first electrode and the second electrode, each of the inductor, the first electrode and the second electrode comprises biometal, and the dielectric comprises a biopolymer having a glass transition temperature in a range of 36~42° C.

The biometal may comprise Mg or Fe, and the biopolymer may comprise PLGA.

The biosensor may further comprise a first sensor protection layer disposed below the inductor and the capacitor, and a second sensor protection layer disposed below the inductor and the capacitor.

A change in a dielectric constant of the dielectric is transmitted to an external device through a resonance frequency change with the inductor, and the external device can measure temperature around the biosensor by measuring the resonance frequency change wirelessly.

The biosensor may be adjacent to a heater to measure temperature of the heater. The heater may be adjacent to a biopatch to heat the biopatch, the biopatch may comprise a polymer film comprising a biopolymer and a drug loaded in the polymer film, and the biosensor can measure heating temperature of the heater on the biopatch.

The biosensor can be inserted into brain tissue together with the biopatch and the heater to be used for treatment of a brain tumor.

A biosensor according to another embodiment of the present inventive concept comprises an inductor and a capacitor connected to the inductor, wherein the capacitor comprises a first electrode, a second electrode facing the first electrode and a dielectric disposed between the first electrode and the second electrode, a change in a dielectric constant of the dielectric is transmitted to an external device through a resonance frequency change with the inductor, and the external device can measure temperature around the biosensor by measuring the resonance frequency change wirelessly.

Each of the inductor, the first electrode and the second electrode may comprise biometal, and the dielectric may comprise a biopolymer having a glass transition temperature in a range of 36~42° C.

The biometal may comprise Mg or Fe, and the biopolymer may comprise PLGA.

A bioelectronic patch device according to one embodiment of the present inventive concept comprises a drug patch comprising a polymer film comprising a biopolymer and a drug loaded in the polymer film, and a heater adjacent to the drug patch to heat the drug patch.

The biopolymer may comprise one or more than one of a bioabsorbable polymer, a biodegradable polymer and a biocompatible polymer. The biopolymer may comprise oxidized to starch. The drug may comprise a first drug chemically combined with the oxidized starch and a second drug physically combined with the oxidized starch. An amount of the first drug can be controlled by controlling an oxidation concentration of the oxidized starch.

The heater may comprise biometal. The biometal may comprise Mg or Fe. The heater may comprise a metal pattern formed of the biometal. The metal pattern may have a plurality of holes. The heater can be controlled wirelessly by an alternating magnetic field. Release of the drug can be controlled by the heater.

The bioelectronic patch device may further comprise a temperature sensor adjacent to the heater to measure temperature of the heater. The temperature sensor may comprise an inductor and a capacitor connected to the inductor, and the capacitor may comprise a first electrode, a second electrode facing the first electrode and a dielectric disposed between the first electrode and the second electrode. Each of the inductor, the first electrode and the second electrode may comprise biometal, and the dielectric may comprise a biopolymer having a glass transition temperature in a range of 36~42° C. The biometal may comprise Mg or Fe, and the biopolymer may comprise PLGA. A dielectric constant of the dielectric changes by a temperature change of the heater, the change in the dielectric constant is transmitted to an external device through a resonance frequency change with the inductor, and the external device can measure temperature of the heater by measuring the resonance frequency change wirelessly.

The bioelectronic patch device can be inserted into brain tissue to be used for treatment of a brain tumor.

A bioelectronic patch device according to another embodiment of the present inventive concept comprises a drug patch comprising a polymer film comprising a biopolymer and a drug loaded in the polymer film, a first protection layer disposed on the drug patch, a heater disposed on the first protection layer and heating the drug patch, a temperature sensor disposed on the first protection layer and spaced apart from the heater and measuring temperature of the heater, and a 10 second protection layer covering the heater and the temperature sensor on the first protection layer.

The first and second protection layers may comprise a biopolymer. The biopolymer may comprise PLA.

Advantageous Effects

A biopatch according to the embodiments of the present inventive concept can be disposed and used in a living body such as a human body. The biopatch can be degraded or absorbed naturally after use. The biopatch can be conformally and strongly adhered to the tissue in the human body such as brain tissue.

A bioheater according to embodiments of the present inventive concept can be disposed and used in a living body such as a human body. The bioheater can be degraded or absorbed naturally after use. The bioheater can be controlled wirelessly and thus is easy to use even if it is disposed in the human body.

A biosensor according to embodiments of the present inventive concept can be disposed and used in a living body such as a human body. The biosensor can be degraded or absorbed naturally after use. The biosensor can be controlled wirelessly and thus is easy to use even if it is disposed in the human body.

A bioelectronic patch device according to embodiments of the present inventive concept can be disposed and used in a living body such as a human body. The bioelectronic patch device can be degraded or absorbed naturally after use. The bioelectronic patch device can be conformally and strongly adhered to the tissue in the human body such as brain tissue. The bioelectronic patch device can effectively deliver the drug to the target position. The bioelectronic patch device can have an excellent effect on the treatment of brain tumors.

DETAILED DESCRIPTION

Figure 1:
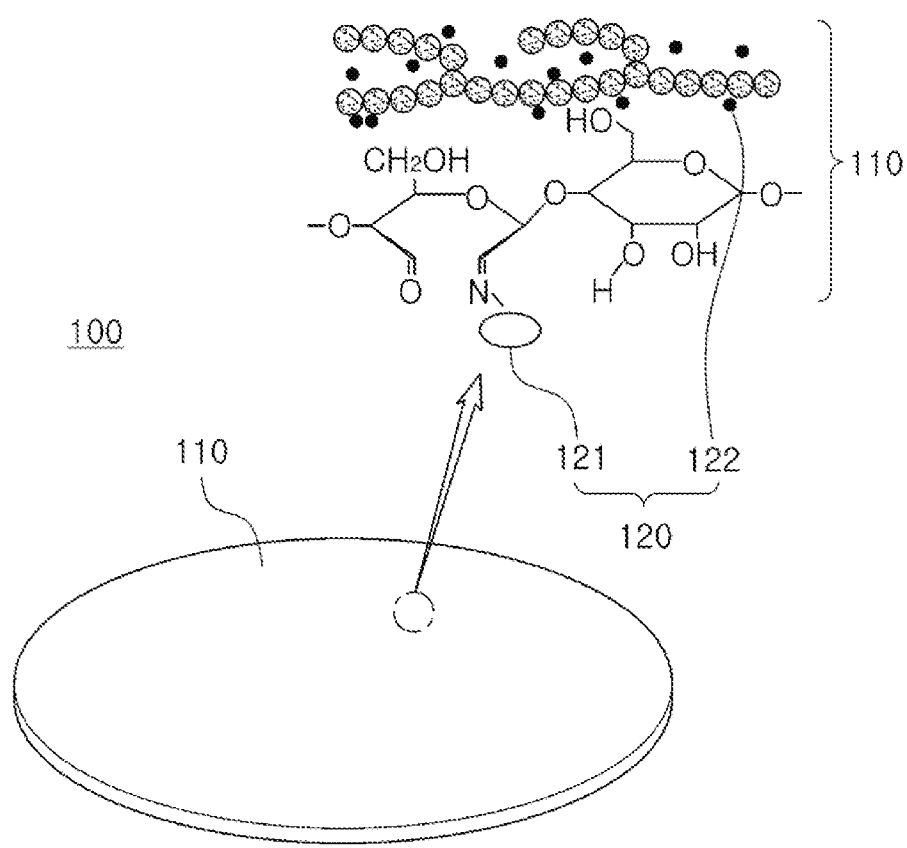
FIG. 1 shows a biopatch according to one embodiment of the present inventive concept.

Hereinafter, a detailed description will be given of the present inventive concept with reference to the following embodiments. The purposes, features, and advantages of the present inventive concept will be easily understood through the following embodiments. The present inventive concept is not limited to such embodiments, but may be modified in other forms. The embodiments to be described below are nothing but the ones provided to bring the disclosure of the present inventive concept to perfection and assist those skilled in the art to completely understand the present inventive concept. Therefore, the following embodiments are not to be construed as limiting the present inventive concept.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. It will be understood that when an element is referred to as being "on" another element, it can be directly on the other element or intervening elements may be present therebetween. In contrast, when an element is referred to as being "directly on" another element, there are no intervening elements present.

The size of the element or the relative sizes between elements in the drawings may be shown to be exaggerated for more clear understanding of the present inventive concept. In addition, the shape of the elements shown in the drawings may be somewhat changed by variation of the manufacturing process or the like. Accordingly, the embodiments disclosed herein are not to be limited to the shapes shown in the drawings unless otherwise stated, and it is to be understood to include a certain amount of variation.

The term "bio" used herein means that it has biodegradable, bioabsorbable and/or biocompatible property and thus can be applied to a living body such as a human body. Accordingly, the terms such as "biopolymer", "biometal", "biopatch", "bioheater", "biosensor" and "bioelectronic patch device" mean that, after being disposed in a living body to be used, they can be degraded and/or absorbed naturally in the living body, or there is no harm or minimum harm even if they remain in the living body.

The terms "biopatch", "bioheater", "biosensor", and "bioelectronic patch device" are described herein as being used for the treatment of brain tumors and being disposed in brain tissue. However, they are not limited to such descriptions, and can be disposed and used in various sites inside living bodies such as a human body and the like for the diseases diagnosis and/or diseases treatment.

[Biopatch]

FIG. 1 shows a biopatch according to one embodiment of the present inventive concept.

Referring to FIG. 1, a biopatch 100 may comprise a polymer film 110 and a drug 120.

The polymer film 110 may comprise a biopolymer. The biopolymer may comprise one or more than one of a bioabsorbable polymer, a biodegradable polymer and a biocompatible polymer.

The bioabsorbable polymer may comprise one or more than one selected from the group consisting of oxidized starch, starch, starch ester, starch ether, alginic acid, carrageenan, chitin, chitosan, chondroitin sulfate, dextran, dextran sulfate, dextrose, glycogen, hyalumonic acid, maltose, pectin, pullulan, avidin, biotin, collagen, elastin, silk, glycerol, phospholipid, triglycerides (TG), polylactic acid (PLA), polyglycolic acid (PGA), poly (D,L-lactic-co-glycolic) acid (PLGA), polycaprolactone (PCL), polydioxanone (PDO), poly-β-hydroxybutyrate (PHB), polytrimethylenecarbonate (PTMC), poly[1,3-bis(p-carboxyphenoxy)propane:sebacic acid](PCPP:SA), poly (sebacic acid), poly(azelaic anhydride), poly-L-lysine, poly-L-glutamic acid, poly-L-alanine, poly-γ-aminobutylic acid (GABA) and polyethylene glycol/polylactic acid (PELA).

The biodegradable polymer may comprise one or more than one selected from the group consisting of agar, cellulose, carboxymethyl cellulose, gum arabic, gum karaya, gum tragacanth, mannan and xanthan gum.

The biocompatible polymer may comprise one or more than one selected from the group consisting of polyethylene glycol (PEG), silicones, natural rubbers, synthetic rubbers, polyisobutylene, neoprenes, polybutadiene, polyisoprenes, polysiloxanes, acrylic copolymers, vinyl acetate, polyacrylates, ethylene vinyl acetates, styrene-isoprene, polyurethanes, polyether amide and styrene-rubber.

It is preferable that the polymer film 110 comprises oxidized starch. The oxidized starch contains an aldehyde group formed by oxidation of an alcohol group of starch. The oxidation concentration of the oxidized starch, namely the number of the aldehyde group and the alcohol group contained in the oxidized starch can be controlled by controlling the oxidation reaction of the starch by an oxidizing agent. When the oxidation concentration is increased, the number of the aldehyde group contained in the oxidized starch increases and the alcohol group decreases. The biopatch 100 can make a covalent bond with brain tissue via the aldehyde group, and make a hydrogen bond with brain tissue via the alcohol group. That is, the biopatch 100 can strongly combine with the brain tissue via the covalent bond and hydrogen bond between the oxidized starch on the surface of the polymer film 110 and the brain tissue. In addition, the biopatch 100 can be adhered conformally along the surface of the brain tissue. Accordingly, the drug 120 in the biopatch 100 can be accurately delivered to a target position around the brain tumor removal site without leaking into normal brain tissue or brain spinal cord.

The drug 120 may comprise a first drug 121 and a second drug 122. The first drug 121 represents a drug chemically combined with the polymer film 110 by reacting with the aldehyde group of the polymer film 110, and the second drug 122 represents a drug physically combined with or loaded in the polymer film 110. By controlling the oxidation concentration of the oxidized starch of the polymer film 110, the number of aldehyde groups in the polymer film 110 can be controlled and the amount of the first drug 121 chemically combined with the polymer film 110 can be controlled. The first drug 121 can be released more slowly than the second drug 122 because the first drug 121 combines strongly with the polymer film 110 in comparison with the second drug 122. The biopatch 100 can extend or control the drug delivery time by controlling the amount of the first drug 121 and/or the second drug 122.

The drug 120 may include various drugs depending on the type of disease and the like. For example, when the biopatch 100 is used for brain tumor treatment, the drug 120 may include an anticancer drug. For example, the anticancer drug may comprise doxorubicin, temozolomide, etc.

The biopatch 100 may have a diameter of about 18 mm and a thickness of about 200 an.

Figure 2:
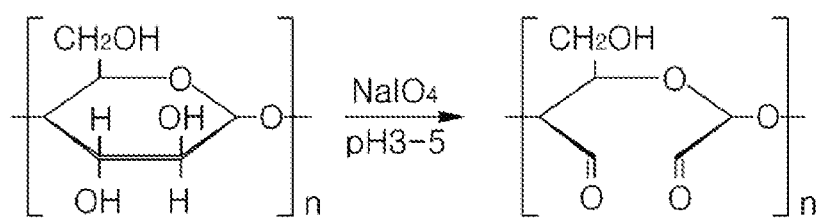
FIG. 2 shows a method of forming a biopatch according to one embodiment of the present inventive concept.
Figure 2:
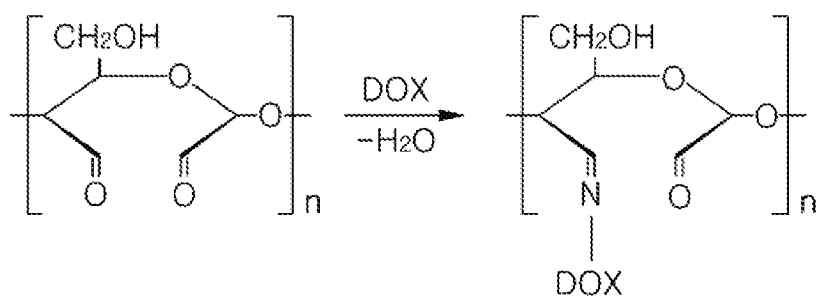

FIG. 2 shows a method of forming a biopatch according to one embodiment of the present inventive concept.

Referring to FIG. 2(a), $NaIO_4$ (sodium periodate) can be used as an oxidizing agent for synthesizing oxidized starch. Starch is added to the solution formed by dissolving 2.14 g of $NaIO_4$ in 250 ml of water, and 35-37% hydrochloric acid is also added to adjust the pH to 3-5. This mixed solution is stirred at 40° C. for one day to form oxidized starch having an aldehyde group. The mixed solution is filtered, washed three times with deionized water and dried at 40° C. for 24 hours under vacuum to form oxidized starch powders.

Referring to FIG. 2(b), 1.5 g of the oxidized starch powders and 50 mg of doxorubicin (DOX) are dissolved in 40 g of water at 80° C. to form a mixed solution. The mixed solution is stirred for 24 hours to form imine linkage between the oxidized starch and doxorubicin (DOX). 0.45 g of glycerol is added to the mixed solution, and after 1 hour, the mixed solution is placed at petridish and dried at 65° C. and 80% humidity for 48 hours to form a biopatch.

By controlling the amount of the oxidized starch powders and/or the amount of the glycerol, the biopatch with various glycerol concentrations can be formed, and the flexibility of the biopatch can be controlled.

By controlling the amount of the oxidized starch powders and/or the amount of the oxidizing agent, the oxidation concentration (or the number of aldehyde groups) of the oxidized starch can be controlled.

By controlling the oxidation concentration, the amount of doxorubicin (DOX) that is chemically combined with the oxidized starch can be controlled. The doxorubicin (DOX) loaded in the biopatch can be divided into a first doxorubicin chemically combined with the oxidized starch and a second doxorubicin physically combined with or loaded in the oxidized starch. Since the second doxorubicin has a weak binding force with the oxidized starch in comparison with the first doxorubicin, the second doxorubicin can be released from the biopatch more rapidly. That is, by controlling the oxidation concentration of the oxidized starch, the amount of the first doxorubicin and the second doxorubicin combined with the oxidized starch can be controlled, and thus the amount and the speed of the doxorubicin released from the biopatch can be controlled. For example, when the amount of the first doxorubicin combined with the oxidized starch is larger than the amount of the second doxorubicin, the amount of doxorubicin released from the biopatch at the initial stage is relatively small, and when the amount of the second doxorubicin is larger than the amount of the first doxorubicin, the amount of doxorubicin released from the biopatch at the initial stage is relatively large. Accordingly, the release amount and release speed of doxorubicin can be controlled by controlling the oxidation concentration of the oxidized starch.

[Bioheater]

Figure 3:
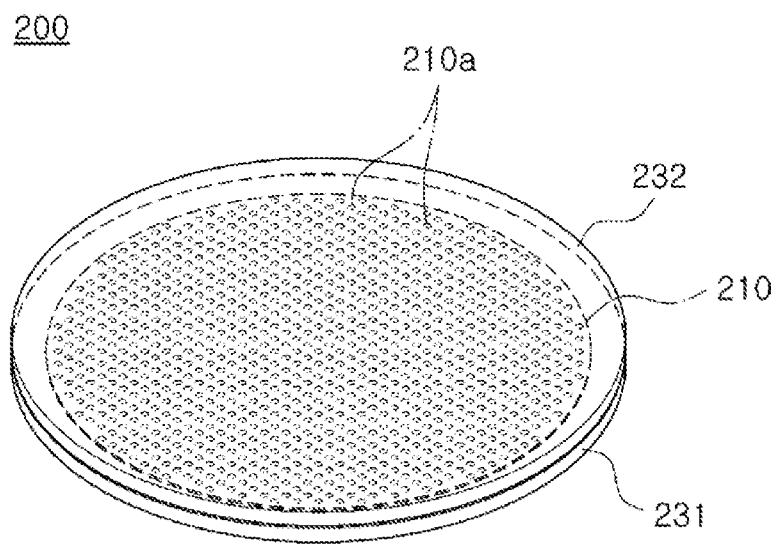
FIG. 3 shows a bioheater according to one embodiment of the present inventive concept.

FIG. 3 shows a bioheater according to one embodiment of the present inventive concept.

Referring to FIG. 3, a bioheater 200 may include a heater 210, a first heater protection layer 231 and a second heater protection layer 232.

The heater 210 may comprise biometal. The biometal may comprise magnesium (Mg) or iron (Fe). The heater 210 may include a metal pattern formed of the biomaterial. The heater 210 may include a plurality of holes 210a. The heater 210 can uniformly generate heat by the holes 210a.

The heater 210 can be controlled wirelessly by an alternating magnetic field. When the alternating magnetic field is provided to the heater 210, the heater 210 can generate heat.

The first heater protection layer 231 and the second heater protection layer 232 may be disposed below and above the heater 210, respectively. The first heater protection layer 231 and the second heater protection layer 232 can protect the heater 210. The first heater protection layer 231 and the second heater protection layer 232 may comprise a biopolymer. For example, the biopolymer may comprise PLA.

Although not shown in the drawing, the bioheater 200 is disposed in the human body, for example, brain tissue together with the biopatch (100 in FIG. 1), and can control drug release of the biopatch. The bioheater 200 can heat the biopatch to promote drug release, and adjust the heating temperature to control the drug release speed.

Figure 4:
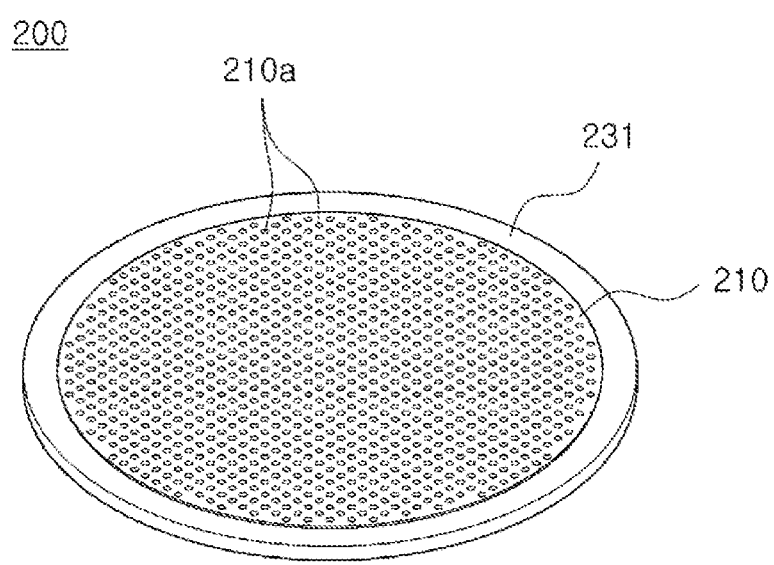
FIG. 4 shows a method of forming a bioheater according to one embodiment of the present inventive concept.

FIG. 4 shows a method of forming a bioheater according to one embodiment of the present inventive concept.

Referring to FIG. 4, a heater 210 is formed on a first heater protection layer 231. The first heater protection layer 231 may be formed of a biopolymer, for example, PLA, on a substrate (not shown) by carrying out a spin coating process.

The heater 210 can be formed as a metal pattern by carrying out a thermal evaporation process to form a metal layer of biometal on the first heater protection layer 231 and then patterning the metal layer. The metal pattern may have a plurality of holes 210a. The biometal may comprise Mg or Fe. The metal layer may have a thickness of about 1.5 an.

The patterning can be carried out by forming a photoresist pattern on the metal layer and then etching an exposed metal layer with an etching solution. The etch solution may contain nitric acid, deionized water and ethylene glycol in a ratio of 1:1:3.

Although not shown in drawing, a metal oxide layer such as ZnO and the like may be formed on the first heater protection layer 231 before forming the metal layer. The metal layer can be effectively formed due to the metal oxide layer. In addition, the heater 210 may be formed directly on the first heater protection layer 231 or may be transferred to the first heater protection layer 231 after being formed elsewhere.

Referring again to FIG. 3, a second heater protection layer 232 covering the heater 210 is formed on the first heater protection layer 231. The second heater protection layer 232 may be formed of a biopolymer, for example, PLA by carrying out a spin coating process.

[Biosensor]

Figure 5:
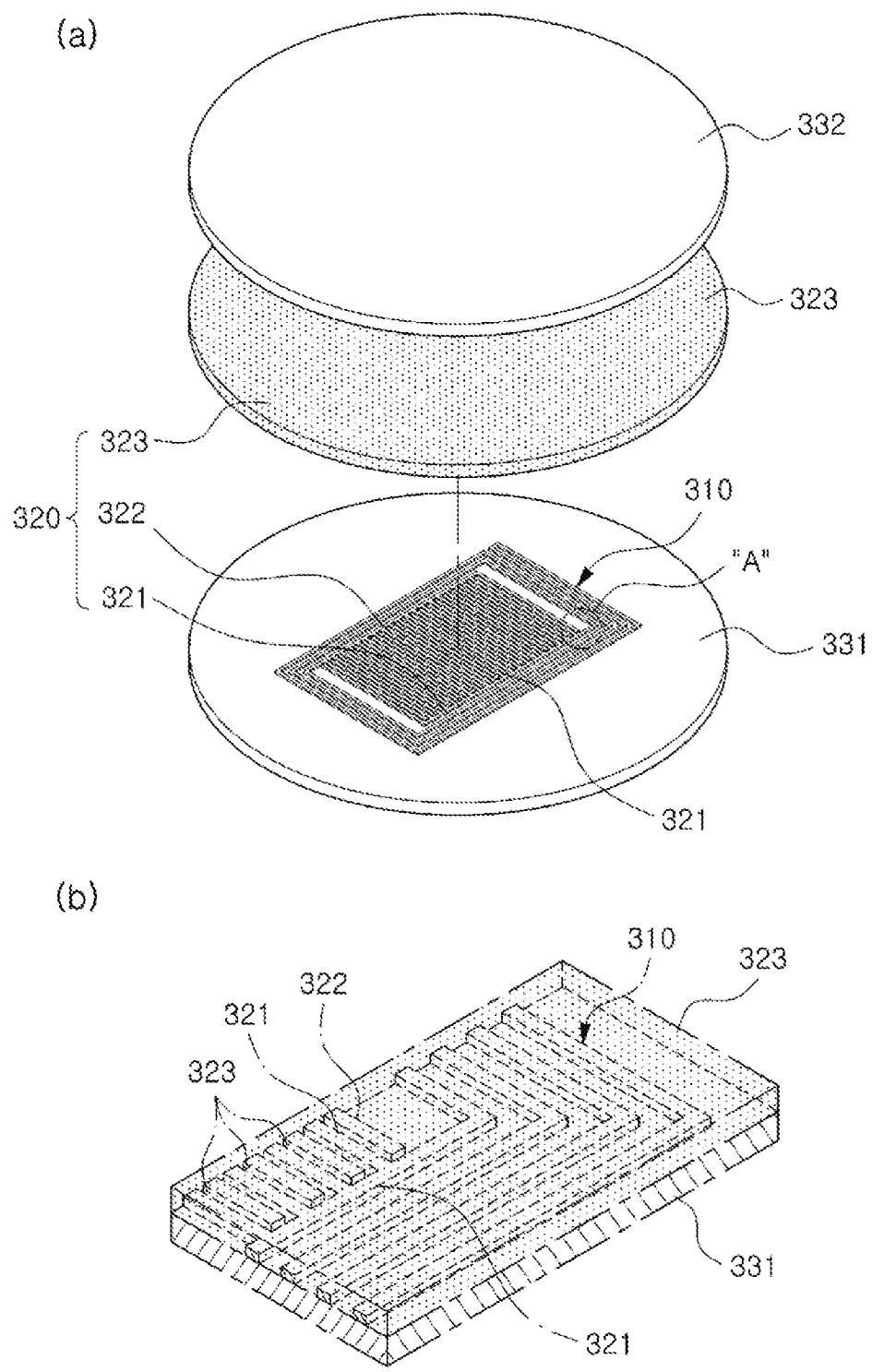
FIG. 5 shows a biosensor according one embodiment of the present inventive concept.
Figure 6:
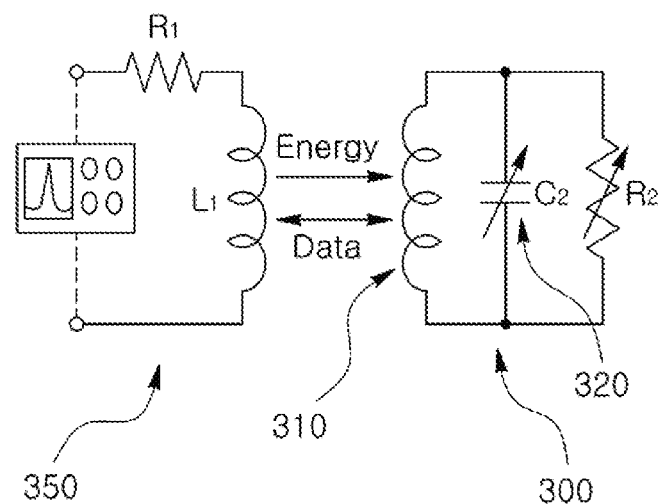
FIG. 6 shows a circuit diagram of a biosensor according to one embodiment of the present inventive concept.

FIG. 5 shows a biosensor according one embodiment of the present inventive concept, and FIG. 6 shows a circuit diagram of a biosensor according to one embodiment of the present inventive concept. FIG. 5(b) shows an enlarged view of area A in FIG. 5(a).

FIGS. 5 and 6, a biosensor 300 may include an inductor 310, a capacitor 320, a first sensor protection layer 331 and a second sensor protection layer 332. In addition, the biosensor 300 may include an LC oscillator having an inductor 310 and a capacitor 320.

The inductor 310 may comprise biometal, for example, Mg or Fe. The inductor 310 may surround the capacitor 320 in a coil shape. The inductor 310 may be connected with the capacitor 320 in parallel.

The capacitor 320 may include a first electrode 321, a second electrode 322 and a dielectric 323. The first electrode 321 and the second electrode 322 may comprise biometal, for example, Mg or Fe. The first electrode 321 and the second electrode 321 may have a comb shape in order to increase the area facing each other. The dielectric 323 may be disposed between the first electrode 321 and the second electrode 322. In the process of formation, the space between the inductor 310 and the capacitor 320 may be filled with the dielectric 323, and the inductor 310 and the capacitor 320 are covered by the dielectric 323. The dielectric 323 may comprises a biopolymer having a glass transition temperature in the range of 36~42° C. The biopolymer may comprise, for example, PLGA (lactic acid:glycolic acid=65:35). The PLGA has a glass transition temperature (Tg) at about 39° C. which is similar to human body temperature. If temperature changes around this glass transition temperature, the dielectric constant of the dielectric 323 is changed. As a result, the capacitance is changed and the resonance frequency is changed. An external device 350 can measure the temperature change by measuring the change of the resonance frequency wirelessly outside the human body where the biosensor 300 is disposed. The biosensor 300 can measure the temperature in real time and the measured temperature can be read wirelessly and monitored by the external device 350.

The first sensor protection layer 331 and the second sensor protection layer 332 may be disposed below and above the heater 210, respectively. The first sensor protection layer 331 and the second sensor protection layer 332 can protect the inductor 310 and the capacitor 320. The first sensor protection layer 331 and the second sensor protection layer 332 may comprise a biopolymer, for example, PLA.

Although not shown in the drawing, the biosensor 300 is disposed in the human body, for example, brain tissue together with the biopatch (100 in FIG. 1) and the bioheater (200 in FIG. 3), and can measure the temperature of the bioheater and can control the bioheater. Accordingly, the damage of the brain tissue resulting from being overheated by the bioheater at temperature higher than 42° C. can be prevented.

Figure 7:
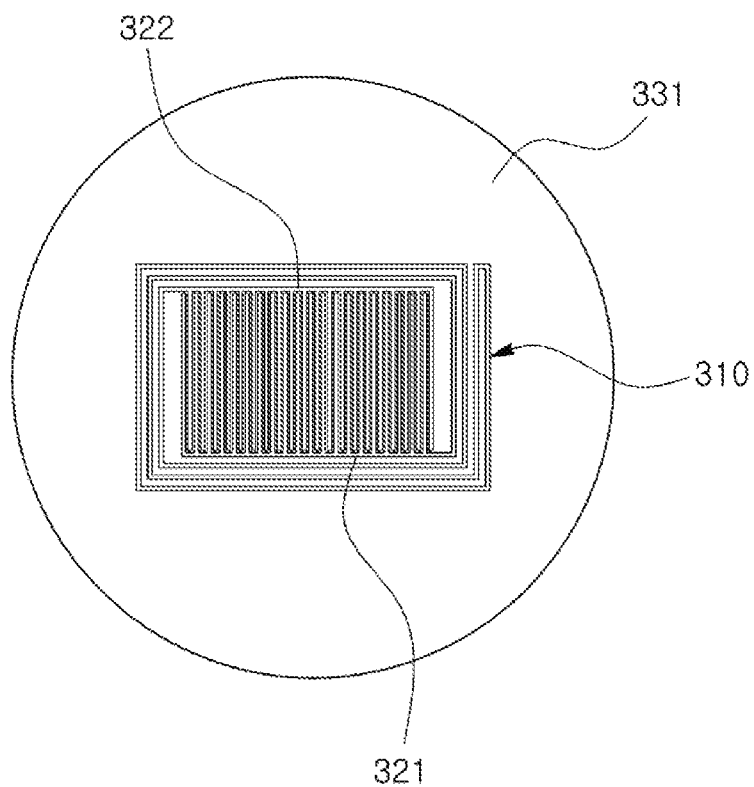
FIGS. 7 and 8 show a method of forming a biosensor according to one embodiment of the present inventive concept.
Figure 8:
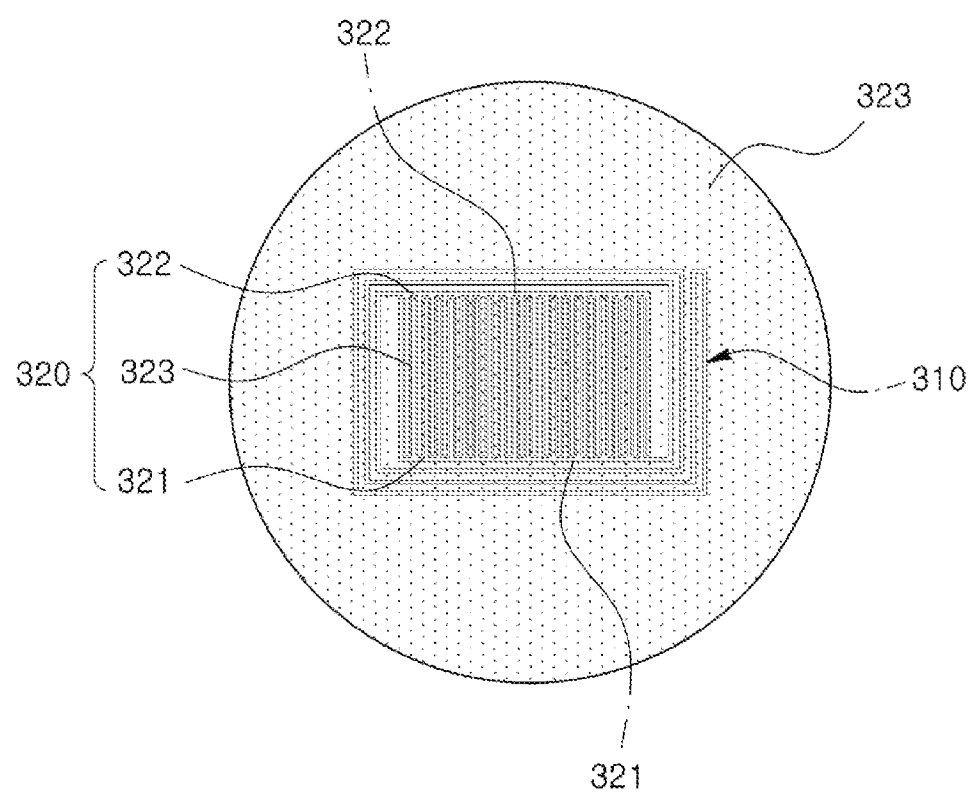

FIGS. 7 and 8 show a method of forming a biosensor according to one embodiment of the present inventive concept.

Referring to FIG. 7, an inductor 310, a first electrode 321 and a second electrode 322 are formed on a first sensor protection layer 331. The first sensor protection layer 331 may be formed of a biopolymer, for example, PLA, on a substrate (not shown) by carrying out a spin coating process.

The inductor 310, the first electrode 321 and the second electrode 322 can be formed as a metal pattern by carrying out a thermal evaporation process to form a metal layer of biometal on the first sensor protection layer 331 and then patterning the metal layer. The biometal may comprise Mg or Fe. The metal layer may have a thickness of about 1.5 µm.

The patterning can be carried out by forming a photoresist pattern on the metal layer and then etching an exposed metal layer with an etching solution. The etch solution may contain nitric acid, deionized water and ethylene glycol in a ratio of 1:1:3.

Although not shown in the drawing, a metal oxide layer such as ZnO and the like may be formed on the first sensor protection layer 331 before forming the metal layer. The metal layer can be effectively formed due to the metal oxide layer. In addition, the inductor 310, the first electrode 321 and the second electrode 322 may be formed directly on the first sensor protection layer 331 or may be transferred to the first sensor protection layer 331 after being formed elsewhere.

A dielectric 323 is formed between the first electrode 321 and the second electrode 322. In the process of formation, the space between the inductor 310 and the capacitor 320 may be filled with the dielectric 323, and the inductor 310 and the capacitor 320 may be covered by the dielectric 323. The dielectric 323 may be formed of a biopolymer having a glass transition temperature in the range of 36~42° C. The biopolymer may comprise, for example, PLGA (lactic acid: glycolic acid=65:35).

Referring again to FIG. 5, a second sensor protection layer 332 covering the inductor 310 and the capacitor 320 is formed on the first sensor protection layer 331. The second sensor protection layer 332 may be formed of a biopolymer, for example, PLA by carrying out a spin coating process.

[Bioelectronic Patch Device]

Figure 9:
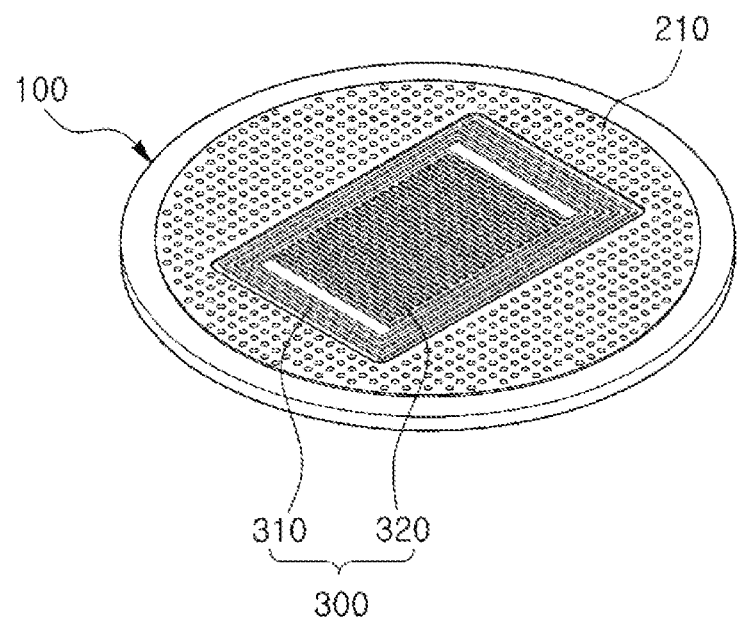
FIG. 9 is a plan view of a bioelectronic patch device according to one embodiment of the present inventive concept.
Figure 10:
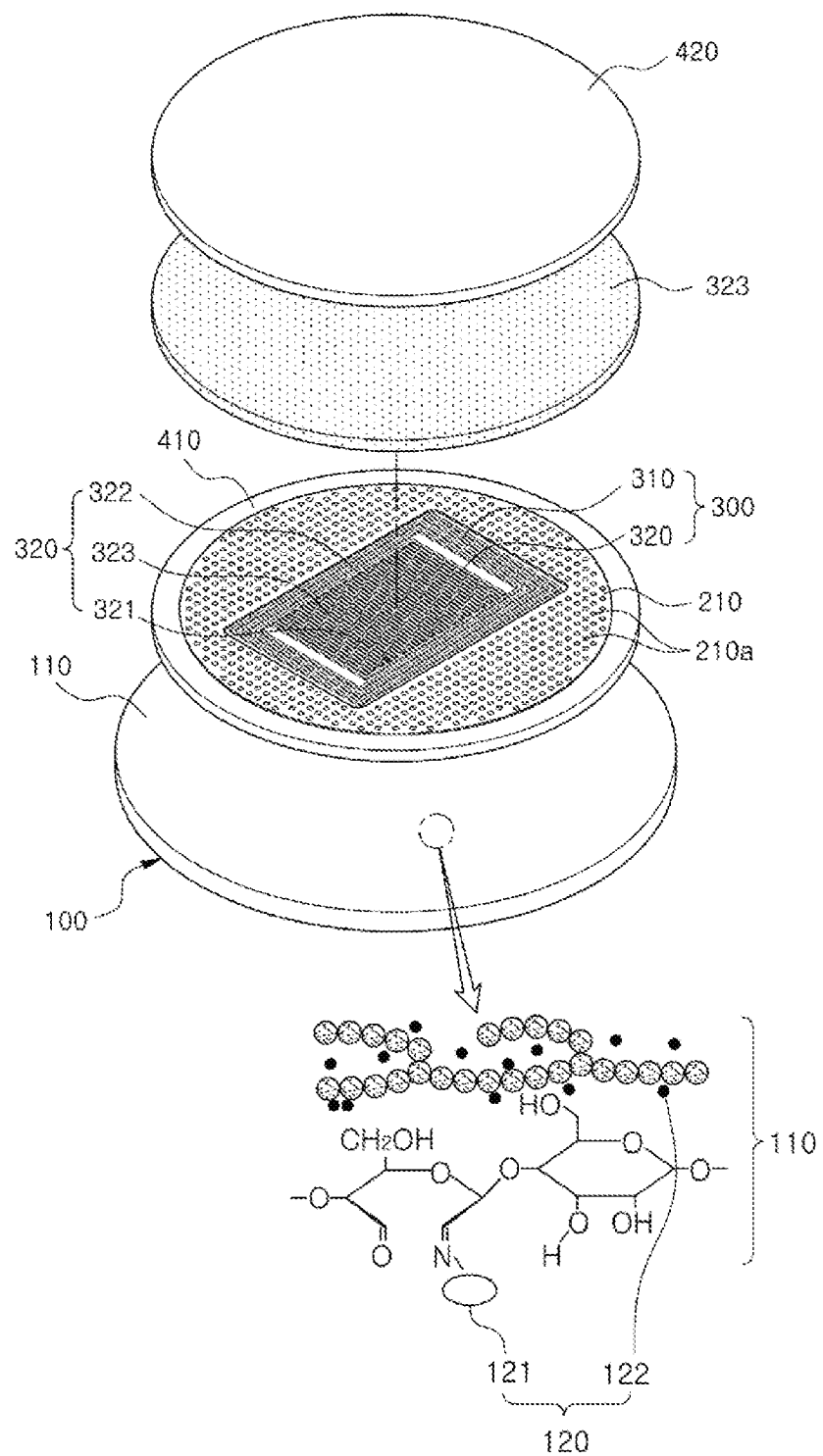
FIG. 10 is an exploded perspective view of the bioelectronic patch device of FIG. 9.

FIG. 9 is a plan view of a bioelectronic patch device according to one embodiment of the present inventive concept and FIG. 10 is an exploded perspective view of the bioelectronic patch device of FIG. 9.

Referring to FIGS. 9 and 10, a bioelectronic patch device 10 may include a drug patch 100, a heater 210, a temperature sensor 300, a first protection layer 410 and a second protection layer 420.

The drug patch 100 may include a polymer film 110 and a drug 120.

The polymer film 110 may comprise a biopolymer. The biopolymer may comprise one or more than one of a bioabsorbable polymer, a biodegradable polymer and a biocompatible polymer.

The bioabsorbable polymer may comprise one or more than one selected from the group consisting of oxidized starch, starch, starch ester, starch ether, alginic acid, carrageenan, chitin, chitosan, chondroitin sulfate, dextran, dextran sulfate, dextrose, glycogen, hyalumonic acid, maltose, pectin, pullulan, avidin, biotin, collagen, elastin, silk, glycerol, phospholipid, triglycerides (TG), Polylactic acid (PLA), polyglycolic acid (PGA), poly (D, L-lactic-co-glycolic) acid (PLGA), Polycaprolactone (PCL), polydioxanone (PDO), poly-β-hydroxybutyrate (PHB), polytrimethylenecarbonate (TMC), poly[1,3-bis(p-carboxyphenoxy)propane:sebacic acid] (PCPP:SA), poly(sebacic acid), poly (azelaic anhydride), poly-L-lysine, poly-L-glutamic acid, poly-L-alanine, poly-γ-aminobutylic acid (GABA) and polyethylene glycol/polylactic acid (PELA).

The biodegradable polymer may comprise one or more than one selected from the group consisting of agar, cellulose, carboxymethyl cellulose, gum arabic, gum karaya, gum tragacanth, mannan and xanthan gum.

The biocompatible polymer may comprise one or more than one selected from the group consisting of polyethylene glycol (PEG), silicones, natural rubbers, synthetic rubbers, polyisobutylene, neoprenes, polybutadiene, polyisoprenes, polysiloxanes, acrylic copolymers, vinyl acetate, polyacrylates, ethylene vinyl acetates, styrene-isoprene, polyurethanes, polyether amide and styrene-rubber.

It is preferable that the polymer film 110 comprises oxidized starch. The oxidized starch comprises an aldehyde group formed by oxidation of an alcohol group of starch. The oxidation concentration of the oxidized starch, namely the number of the aldehyde group and the alcohol group contained in the oxidized starch can be controlled by controlling the oxidation reaction of the starch by an oxidizing agent. When the oxidation concentration is increased, the number of the aldehyde group contained in the oxidized starch increases and the alcohol group decreases. The drug patch 100 can make a covalent bond with brain tissue via the aldehyde group, and make a hydrogen bond with brain tissue via the alcohol group. That is, the drug patch 100 can strongly combine with the brain tissue via the covalent bond and hydrogen bond between the oxidized starch on the surface of the polymer film 110 and the brain tissue. In addition, the drug patch 100 can be adhered conformally along the surface of the brain tissue. Accordingly, the drug 120 in the drug patch 100 can be accurately delivered to a target position around the brain tumor removal site without leaking into normal brain tissue or brain spinal cord.

The drug 120 may comprise a first drug 121 and a second drug 122. The first drug 121 represents a drug chemically combined with the polymer film 110 by reacting with the aldehyde group of the polymer film 110, and the second drug 122 represents a drug physically combined with or loaded in the polymer film 110. By controlling the oxidation concentration of the oxidized starch of the polymer film 110, the number of aldehyde groups in the polymer film 110 can be controlled and the amount of the first drug 121 chemically combined with the polymer film 110 can be controlled. The first drug 121 can be released more slowly than the second drug 122 because the first drug 121 combines strongly with the polymer film 110 in comparison with the second drug 122. The drug patch 100 can extend or control the drug delivery time by controlling the amount of the first drug 121 and/or the second drug 122.

The drug 120 may include various drugs depending on the type of disease and the like. For example, when the drug patch 100 is used for brain tumor treatment, the drug 120 may include an anticancer drug. For example, the anticancer drug may comprise doxorubicin, temozolomide, etc.

The biopatch 100 may have a diameter of about 18 mm and a thickness of about 200 mi.

The heater 210 may be disposed on the drug patch 100. The heater 210 may comprise biometal. The biometal may comprise Mg or Fe. The heater 210 may include a plurality of holes 210a. The eater 210 can uniformly generate heat by the holes 210a.

The heater 210 can be controlled wirelessly by an alternating magnetic field. When the alternating magnetic field is provided to the heater 210, the heater 210 can generate heat.

The heater 210 can control the drug release of the drug patch 100. The heater 210 can heat the drug patch 100 to promote the drug release, and adjust the drug release speed by controlling the heating temperature.

The temperature sensor 300 may be adjacent to the heater 210 on the drug patch 100. The temperature sensor 300 can measure the temperature of the heater 210. The temperature sensor 300 may be disposed in the central region of the heater 210 in order to accurately and effectively measure the temperature of the heater 210. The central region of the heater 210 may be removed in order that the temperature sensor 300 can be disposed. The heater 210 may be ring-shaped.

The temperature sensor 300 may include an inductor 310 and a capacitor 320. In addition, the temperature sensor 300 may include an LC oscillator having an inductor 310 and a capacitor 320.

The inductor 310 may comprise biometal, for example, Mg or Fe. The inductor 310 may surround the capacitor 320 in a coil shape. The inductor 310 may be connected with the capacitor 320 in parallel.

The capacitor 320 may include a first electrode 321, a second electrode 322 and a dielectric 323. The first electrode 321 and the second electrode 322 may comprise biometal, for example, Mg or Fe. The first electrode 321 and the second electrode 321 may have a comb shape in order to increase the area facing each other. The dielectric 323 may be disposed between the first electrode 321 and the second electrode 322. In the process of formation, the space between the inductor 310 and the capacitor 320 and the space between the inductor 310 and the heater 210 may be filled with the dielectric 323, and the inductor 310, the capacitor 320 and the heater 210 are covered by the dielectric 323. The dielectric 323 may comprises a biopolymer having a glass transition temperature in the range of 36~42° C. The biopolymer may comprise, for example, PLGA (lactic acid:glycolic acid=65:35). The PLGA has a glass transition temperature (Tg) at about 39° C. which is similar to human body temperature. If temperature changes around this glass transition temperature, the dielectric constant of the dielectric 323 is changed. As a result, the capacitance is changed and the resonance frequency is changed. An external device (350 in FIG. 6) can measure the temperature change by measuring the change of the resonance frequency wirelessly outside the human body where the temperature sensor 300 is disposed. The temperature sensor 300 can measure the temperature in real time and the measured temperature can be read wirelessly and monitored by the external device.

The temperature sensor 300 can measure the temperature of the heater 210 and can control the heater 210. Accordingly, the damage of the brain tissue resulting from being overheated by the bio heater at temperature higher than 42° C. can be prevented.

The first protection layer 410 may be disposed between the heater 210 and the temperature sensor 300, and the drug patch 100. The second protection layer 420 may be disposed on the heater 210 and the temperature sensor 300. The first protection layer 410 and the second protection layer 420 can protect the heater 210 and the temperature sensor 300. The first protection layer 410 and the second protection layer 420 may comprise a biopolymer, for example, PLA.

FIG. 11 to FIG. 16 show a method of forming a bioelectronic patch device according to one embodiment of the present inventive concept.

Figure 11:
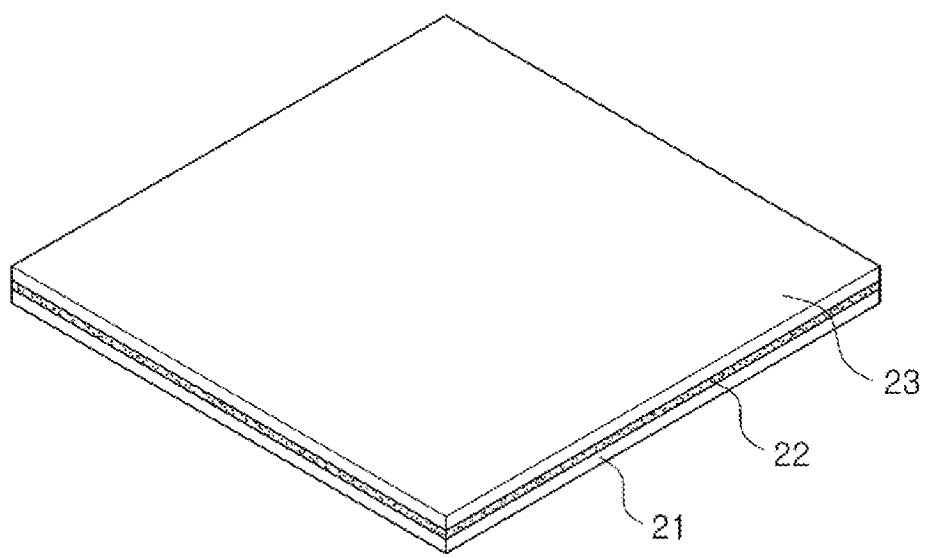
FIG. 11 to FIG. 16 show a method of forming a bioelectronic patch device according to one embodiment of the present inventive concept.

Referring to FIG. 11, a sacrificial layer 22 is formed on a sacrificial substrate 21. The sacrificial substrate 21 may be a silicon substrate. The sacrificial layer 22 may be formed of PMMA (poly(methyl methacrylate)) by carrying out a spin coating process.

A first polyimide layer 23 is formed on the sacrificial layer 22. The first polyimide layer 23 may be formed of polyimide by carrying out a spin coating process.

Figure 12:
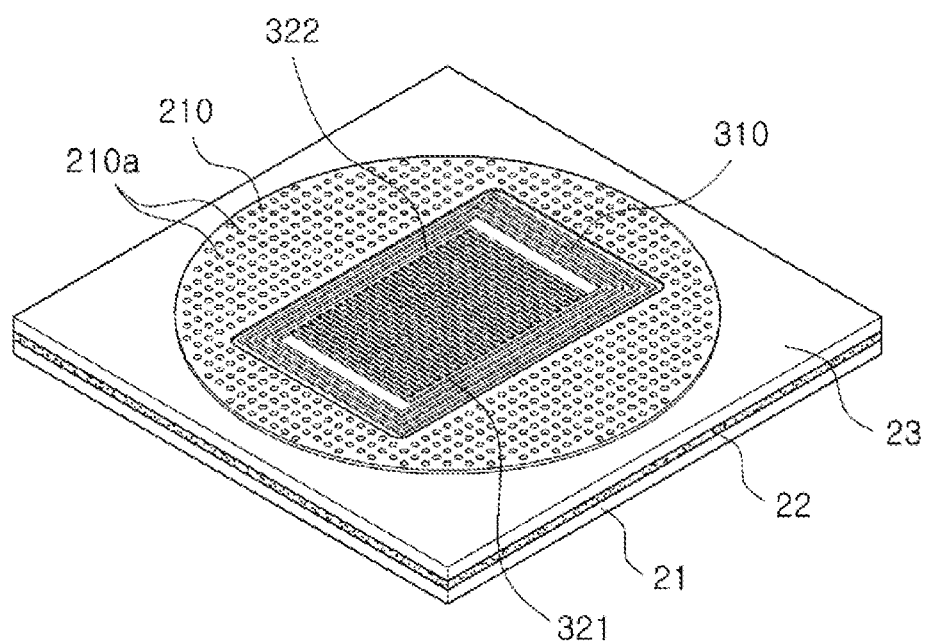

Referring to FIG. 12, a metal pattern including a heater 210, an inductor 310, a first electrode 321 and a second electrode 322 is formed on the first polyimide layer 23. The metal pattern can be formed by carrying out a thermal evaporation process to form a metal layer of biometal on the first polyimide layer 23 and then patterning the metal layer.

The heater 210 may have a plurality of holes 210a. The biometal may comprise Mg or Fe. The metal layer may have a thickness of about 1.5 μm.

The patterning can be carried out by forming a photoresist pattern on the metal layer and then etching an exposed metal layer with an etching solution. The etch solution may contain nitric acid, deionized water and ethylene glycol in a ratio of 1:1:3.

Although not shown in the drawing, a metal oxide layer such as ZnO and the like may be formed on the first polyimide layer 23 before forming the metal layer. The metal layer can be effectively formed due to the metal oxide layer.

Figure 13:
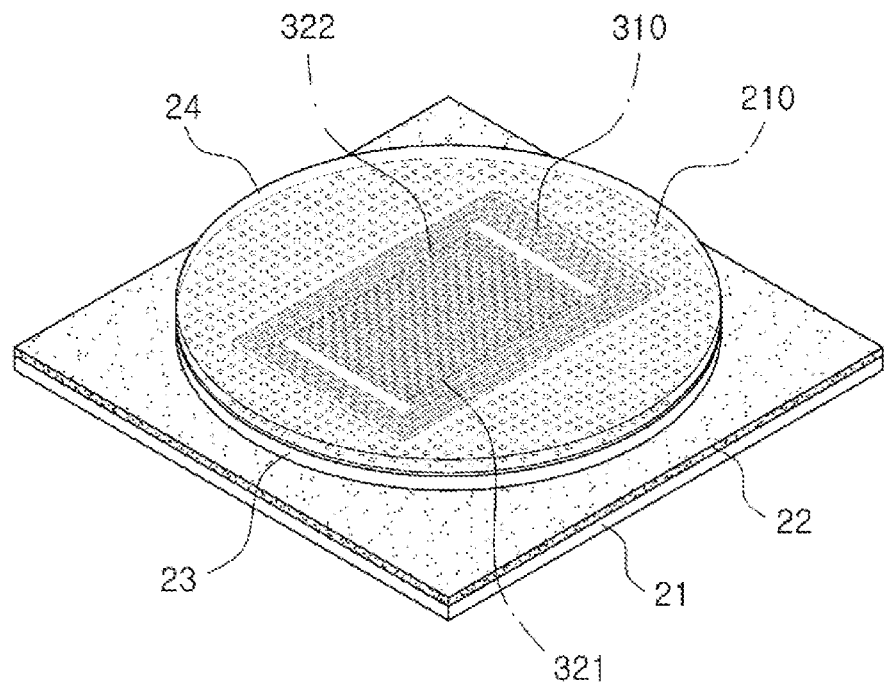

Referring to FIG. 13, a second polyimide layer 24 covering the metal pattern is formed on the first polyimide layer 23. The second polyimide layer 24 can be formed by carrying out a spin coating process to form a polyimide layer and then patterning it. At this time, the first polyimide layer 23 may also be patterned in the same shape as the second polyimide layer 24.

Figure 14:
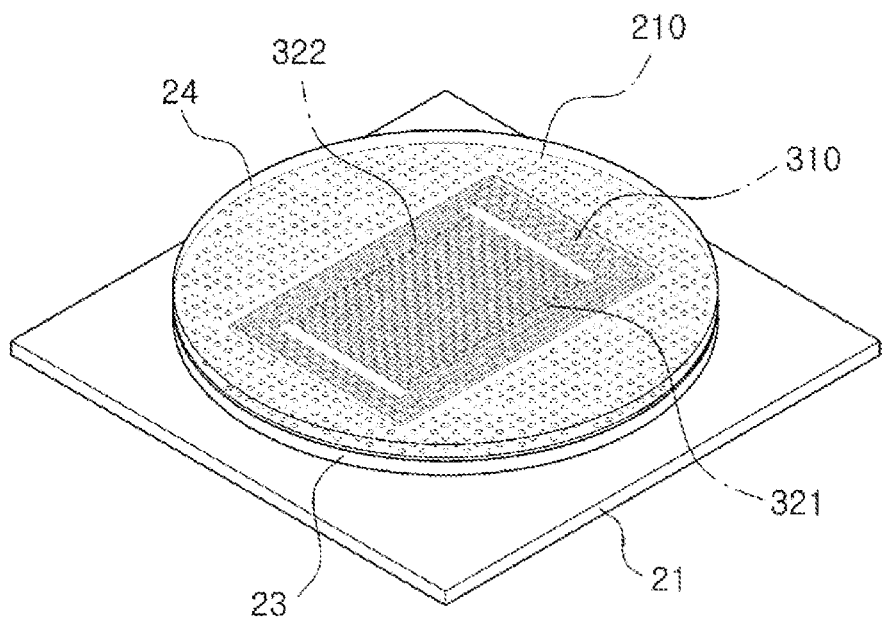

Referring to FIG. 14, the sacrificial layer 22 is removed to separate the laminated structure of the first polyimide layer 23, the metal pattern and the second polyimide layer 24 from the sacrificial substrate 21.

Figure 15:
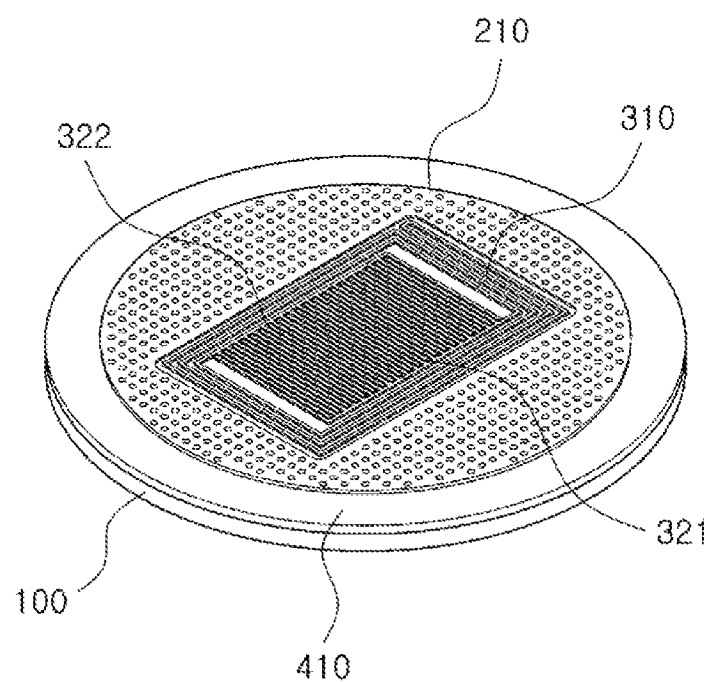

Referring to FIG. 15, the metal pattern is transferred onto the drug patch 100 where the first protective layer 410 is formed. After the metal pattern is picked up by a stamp, the first polyimide layer 23 is removed. After the metal pattern is disposed on the first protective layer 410, the second polyimide layer 24 is removed.

The drug patch 100 may be formed using a biopolymer such as oxidized starch and the like, and a drug such as doxorubicin and the like. Starch is added to the solution formed by dissolving 2.14 g of $NaIO_4$ in 250 ml of water, and 35-37% hydrochloric acid is also added to adjust the pH to 3-5. This mixed solution is stirred at 40° C. for about one day to form oxidized starch having an aldehyde group. The mixed solution is filtered, washed three times with deionized water and dried at 40° C. for 24 hours under vacuum to form oxidized starch powders. 1.5 g of the oxidized starch powders and 50 mg of doxorubicin are dissolved in 40 g of water at 80° C. to form a mixed solution. The mixed solution is stirred for 24 hours to form imine linkage between the oxidized starch and doxorubicin. 0.45 g of glycerol is added to the mixed solution, and after 1 hour, the mixed solution is placed at petridish and dried at 65° C. and 80% humidity for 48 hours to form the drug patch 100.

By controlling the amount of the oxidized starch powders and/or the amount of the glycerol, the drug patch 100 with various glycerol concentrations can be formed, and the flexibility of the drug patch 100 can be controlled.

By controlling the amount of the oxidized starch powders and/or the amount of the oxidizing agent, the oxidation concentration (or the number of aldehyde groups) of the oxidized starch can be controlled.

By controlling the oxidation concentration, the amount of doxorubicin that is chemically combined with the oxidized starch can be controlled. The doxorubicin loaded in the biopatch can be divided into a first doxorubicin chemically combined with the oxidized starch and a second doxorubicin physically combined with or loaded in the oxidized starch. Since the second doxorubicin has a weak binding force with the oxidized starch in comparison with the first doxorubicin, the second doxorubicin can be released from the biopatch more rapidly. That is, by controlling the oxidation concentration of the oxidized starch, the amount of the first doxorubicin and the second doxorubicin combined with the oxidized starch can be controlled, and thus the amount and the speed of the doxorubicin released from the biopatch can be controlled. For example, when the amount of the first doxorubicin combined with the oxidized starch is larger than the amount of the second doxorubicin, the amount of doxorubicin released from the biopatch at the initial stage is relatively small, and when the amount of the second doxorubicin is larger than the amount of the first doxorubicin, the amount of doxorubicin released from the biopatch at the initial stage is relatively large. Accordingly, the release amount and release speed of doxorubicin can be controlled by controlling the oxidation concentration of the oxidized starch.

The first protection layer 410 may be formed of a biopolymer, for example, PLA by carrying out a spin coating process.

Figure 16:
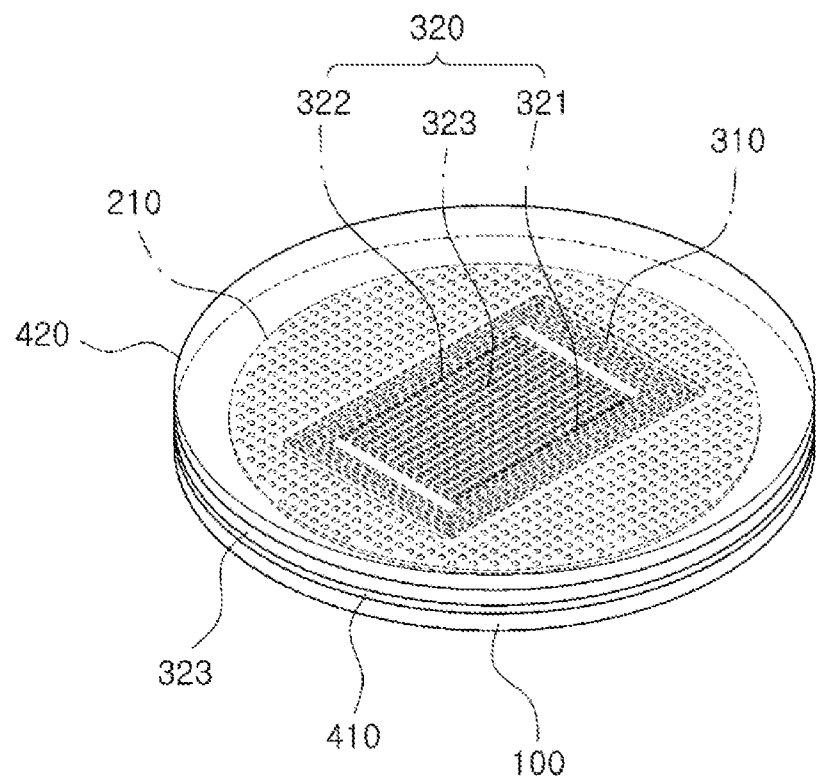

Referring to FIG. 16, a dielectric 323 is formed between the first electrode 321 and the second electrode 322. In the process of formation, the space between the inductor 310 and the capacitor 320, and the space between the inductor 310 and the heater 210 may be filled with the dielectric 323, and the inductor 310, the capacitor 320 and the heater 210 are covered by the dielectric 323. The dielectric 323 may be formed of a biopolymer having a glass transition temperature in a range of 36~42° C. by carrying out a spin coating process. The biopolymer may comprise, for example, PLGA (lactic acid:glycolic acid=65:35).

A second protection layer 420 covering the heater 210 and the temperature sensor 300 is formed on the first protection layer 410. The second protection layer 420 may be formed of a biopolymer, for example, PLA by carrying out a spin coating process.

Figure 17:
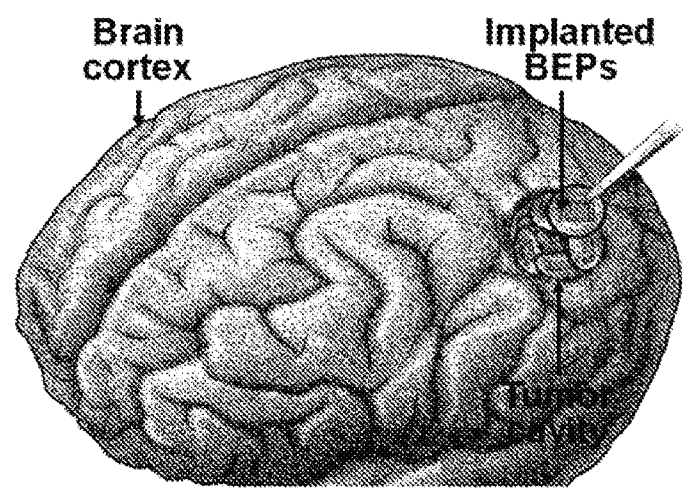
FIG. 17 shows a state in which a bioelectronic patch device according to one embodiment of the present inventive concept that is applied to a human brain.
Figure 18:
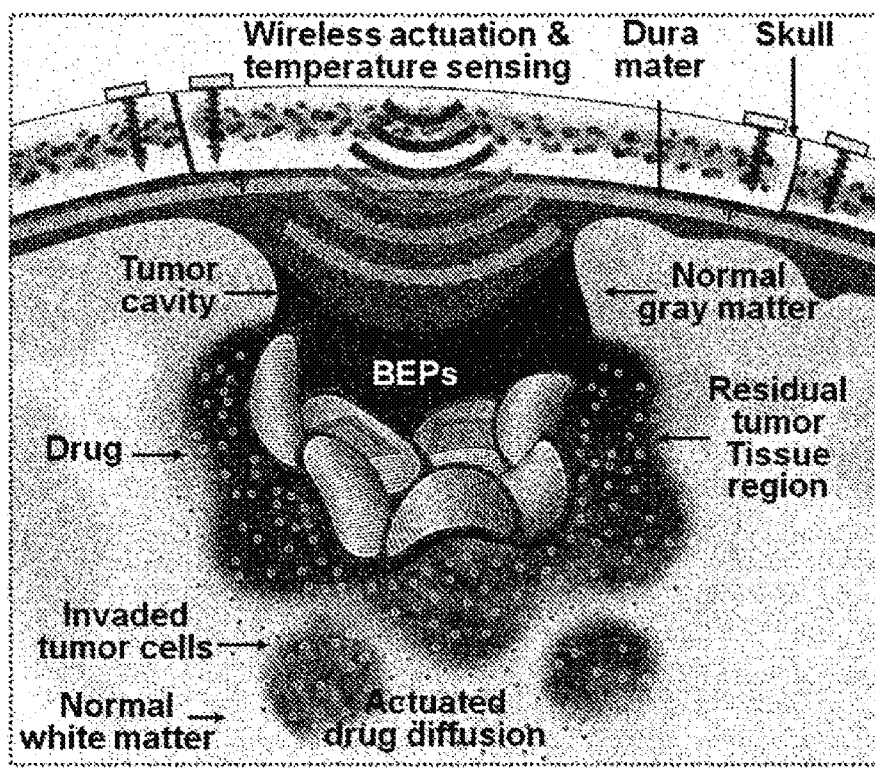
FIG. 18 is an enlarged view of area A in FIG. 17.

FIG. 17 shows a state in which a bioelectronic patch device according to one embodiment of the present inventive concept that is applied to a human brain, and FIG. 18 is an enlarged view of area A in FIG. 17.

Referring to FIGS. 17 and 18, a bioelectronic patch device (BEP) can be attached to a cavity-shaped surgical site after removal surgery of a malignant brain tumor. Because of the stickiness and flexibility of the drug patch of the bioelectronic patch device (BEP), the bioelectronic patch device (BEP) can be conformally and strongly attached to a curved surface of brain's cavity.

The heater of the bioelectronic patch device (BEP) can be operated wirelessly by an alternating magnetic field to heat the drug patch so that it can increase drug release speed of drug patch and drug penetration depth into brain tissue.

The temperature sensor of the bioelectronic patch device (BEP) can monitor the temperature of the heater and prevent the brain tissue from being overheated.

Figure 19:
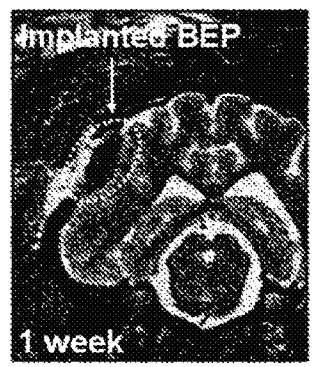
FIG. 19 shows a change with time after a bioelectronic patch device according to one embodiment of the present inventive concept is attached to the brain of a dog.
Figure 19:
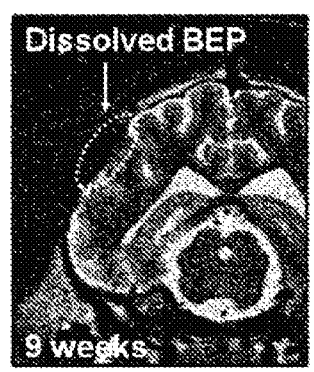

FIG. 19 shows a change with time after a bioelectronic patch device according to one embodiment of the present inventive concept is attached to the brain of a dog. FIG. 19(a) shows an image one week after attaching the bioelectronic patch device and FIG. 19(b) shows an image nine weeks after attaching the bioelectronic patch device. Referring to FIG. 19, the bioelectronic patch device is gradually hydrolyzed and absorbed over time, and thus its size gradually decreases.

Figure 20:
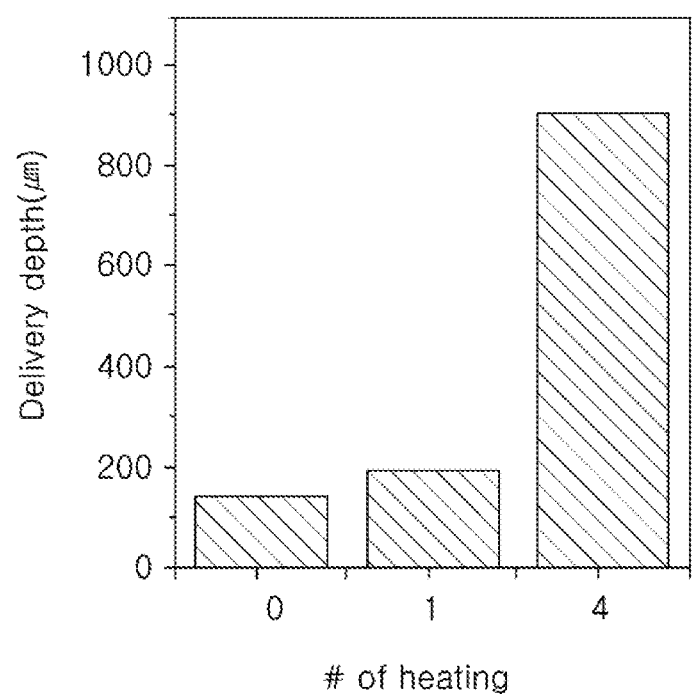
FIG. 20 shows drug delivery depth according to the heating of a bioelectronic patch device according to one embodiment of the present inventive concept.

FIG. 20 shows drug delivery depth according to the heating of a bioelectronic patch device according to one embodiment of the present inventive concept. Referring to FIG. 20, drug penetration depth into the brain tissue is increased by the heating of the heater.

Figure 21:
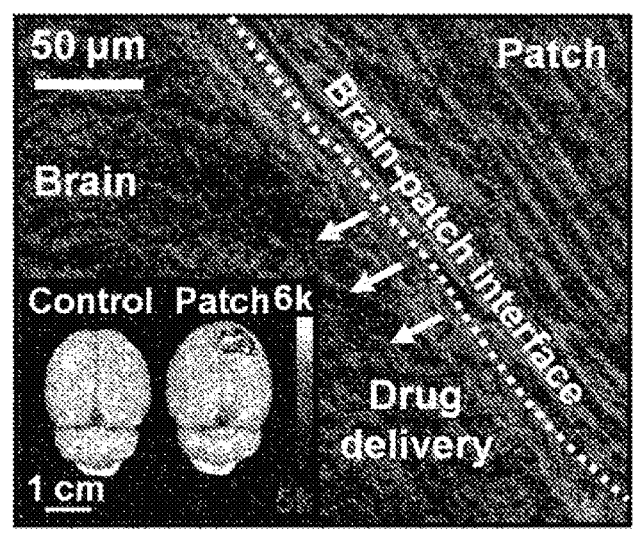
FIG. 21 shows a fluorescence microscope image of an adhesive interface between a brain and a bioelectronic patch device according to one embodiment of the present inventive concept.

FIG. 21 shows a fluorescence microscope image of an adhesive interface between a brain and a bioelectronic patch device according to one embodiment of the present inventive concept. Referring to FIG. 21, a drug patch of the bioelectronic patch device is conformally adhered to the brain tissue, and the drug can be delivered to the brain tissue without leaking into brain spinal cord and the like.

Figure 22:
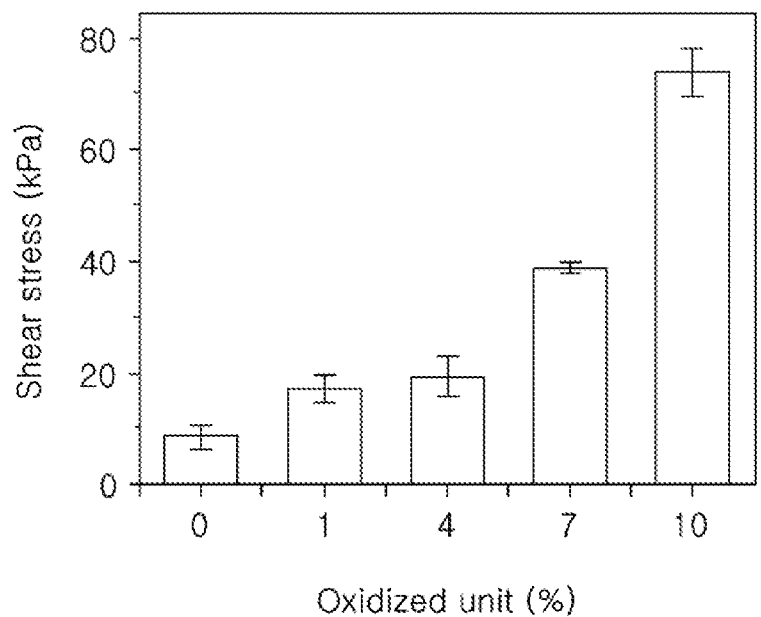
FIG. 22 shows the adhesive shear stress of a drug patch of a bioelectronic patch device according to one embodiment of the present inventive concept.

FIG. 22 shows the adhesive shear stress of a drug patch of a bioelectronic patch device according to one embodiment of the present inventive concept Referring to FIG. 22, oxidized starch exhibits the adhesive shear stress stronger than normal starch. In addition, as the oxidation concentration of oxidized starch increases, the adhesive sheer stress also increases. By the adhesive sheer stress, the drug patch can make a conformal adhesion to brain tissue and this leads to more effective drug delivery.

Figure 23:
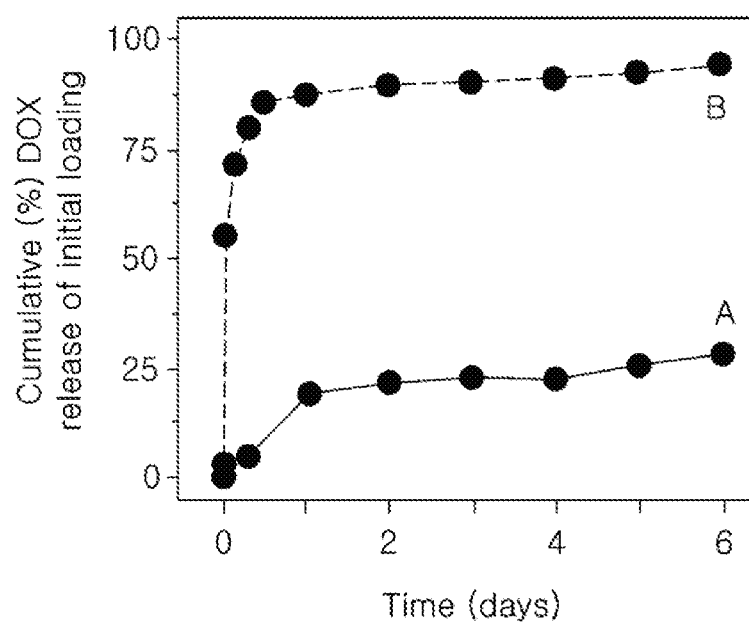
FIG. 23 and FIG. 24 show the cumulative amount of drug release of a bioelectronic patch device according to one embodiment of the present inventive concept.
Figure 24:
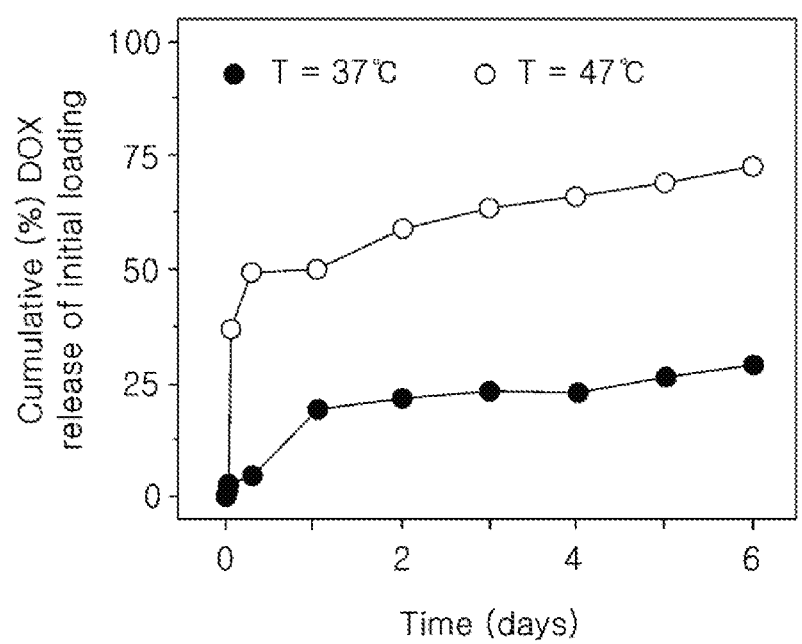

FIG. 23 and FIG. 24 show the cumulative amount of drug release of a bioelectronic patch device according to one embodiment of the present inventive concept. A solid line graph (A) of FIG. 23 represents a drug patch formed of oxidized starch, and a dotted line graph (B) represents a drug patch formed of normal starch. Referring to FIG. 23, the drug in the drug patch formed of the normal starch is physically loaded so that a large amount of drugs is released at the initial stage. However, since the drug in the drug patch formed of the oxidized starch is chemically combined with the oxidized starch, the physically combined drug is released at the initial stage and the chemically combined drug can be released slowly. FIG. 24 shows drug release according to temperature. Referring to FIG. 24, the drug patch of the bioelectronic patch device can release more drugs at 42° C. than at 37° C. That is, as the heating temperature for the drug patch increases, the drug release amount increases. Therefore, the drug release amount can be controlled by controlling the heating temperature of the drug patch.

Figure 25:
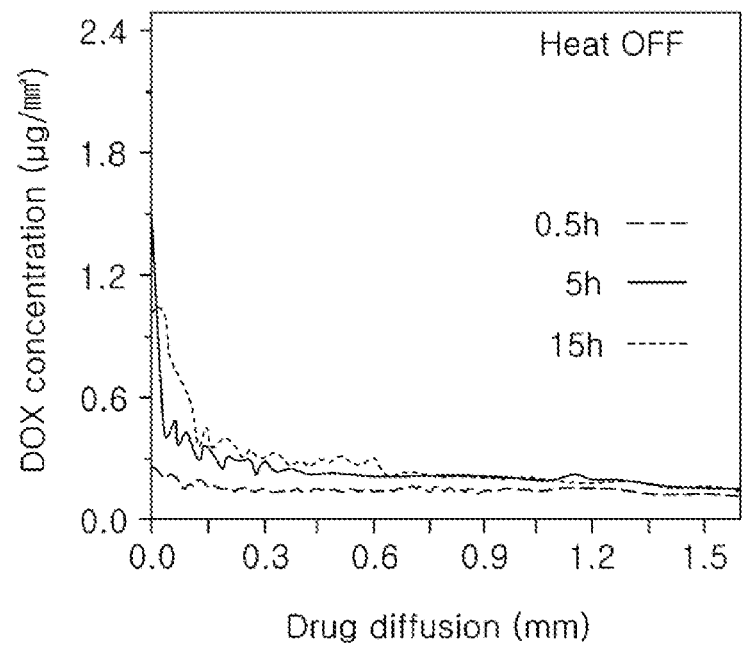
FIG. 25 shows the effect of heating on drug delivery.
Figure 25:
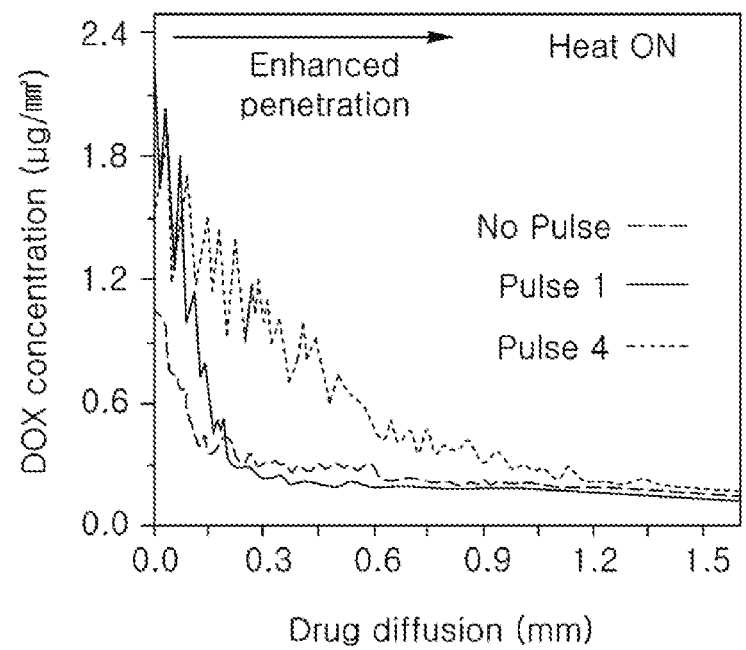

FIG. 25 shows the effect of heating on drug delivery. FIG. 25(a) shows drug delivery when the drug patch is not heated, and FIG. 25(b) shows drug delivery when the drug patch is heated. Referring to FIG. 25, in comparison to the case of not heating the drug patch, both of the drug diffusion amount and the drug diffusion depth are larger when heating the drug patch.

Figure 26:
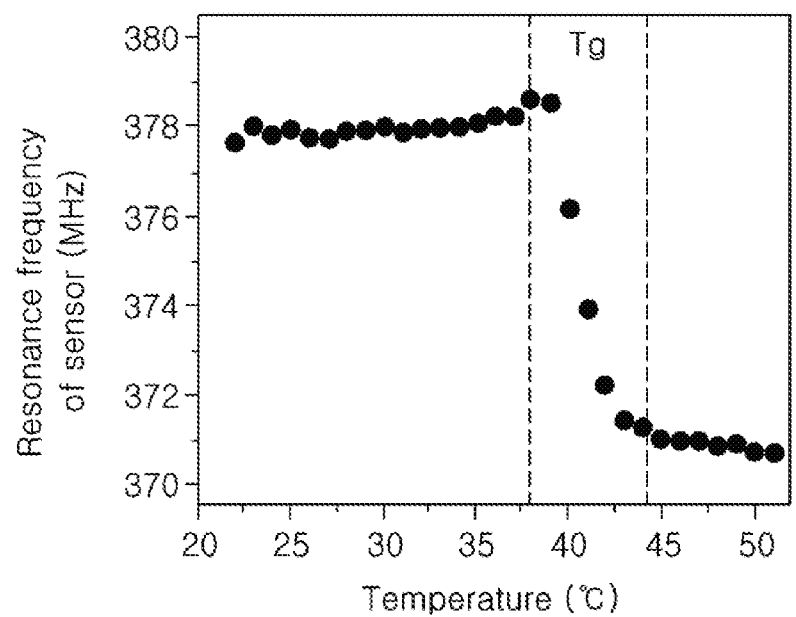
FIG. 26 shows resonance frequency of a biosensor according to temperature.

FIG. 26 shows resonance frequency of a biosensor according to temperature. The biosensor includes a dielectric formed of PLGA (lactic acid:glycolic acid=65:35) having a glass transition temperature of about 39° C. Referring to FIG. 26, if temperature changes around the glass transition temperature (39° C.), the dielectric constant of the dielectric is changed. As a result, the capacitance is changed and the resonance frequency is changed. The temperature change can be measured by measuring the change of the resonance frequency.

Figure 27:
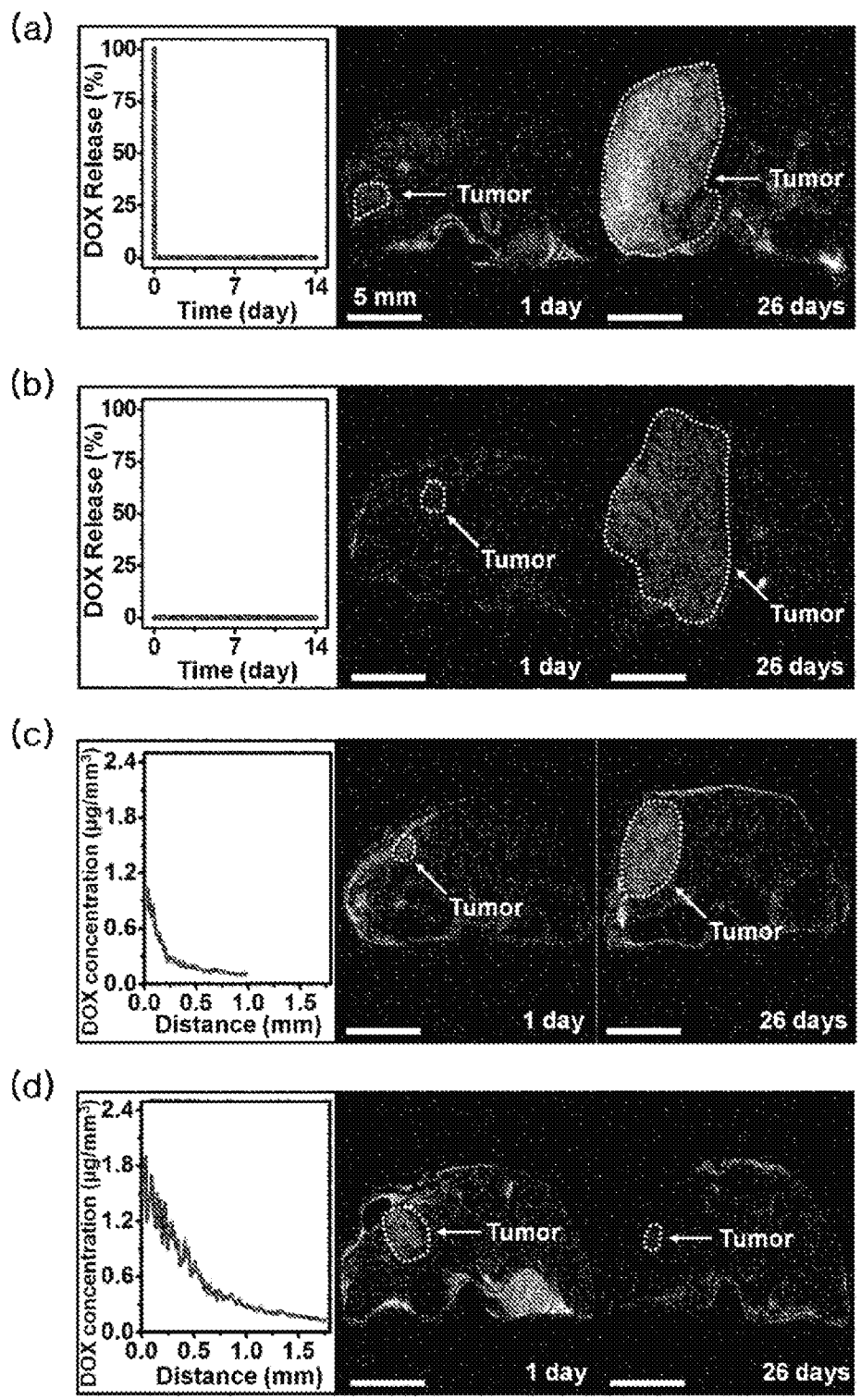
FIGS. 27 to 29 show the result of comparing the size change in brain tumor and the survival rate according to four treatment methods applied to rats having brain tumors.
Figure 28:
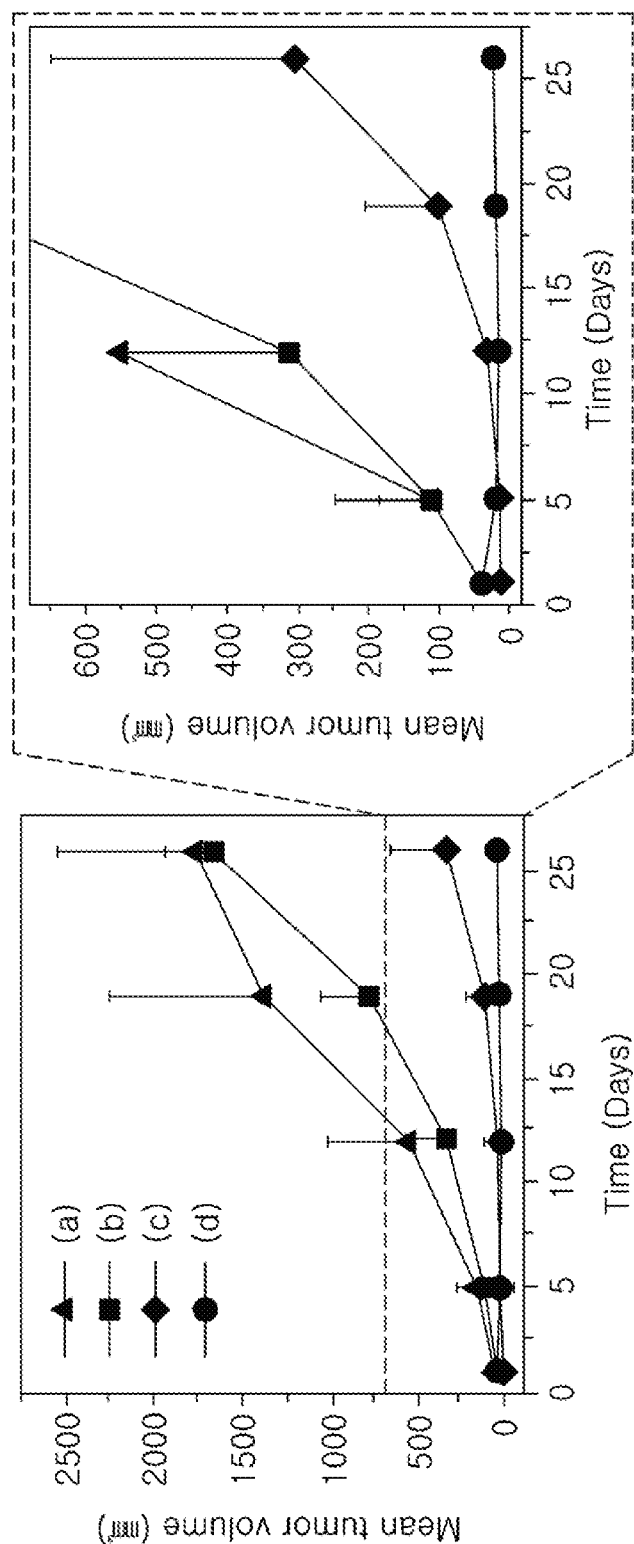
Figure 29:
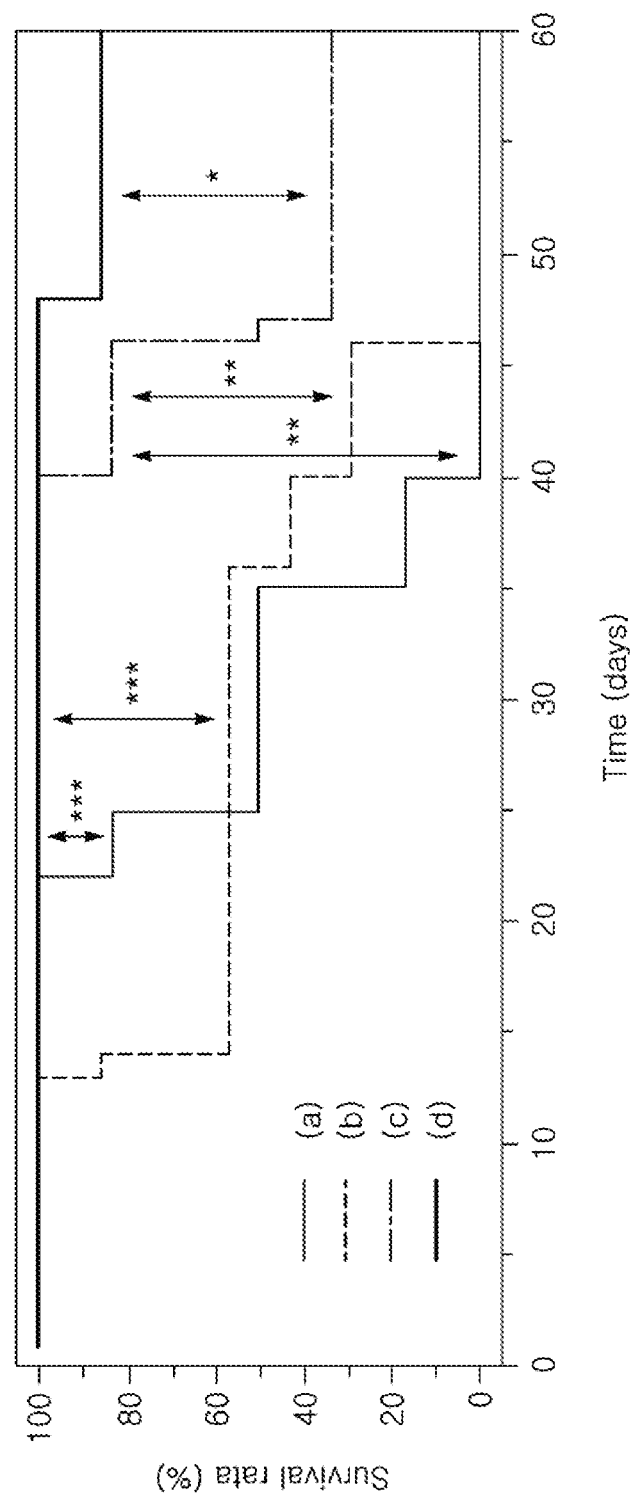

FIGS. 27 to 29 show the result of comparing the size change in brain tumor and the survival rate according to four treatment methods applied to rats having brain tumors. In FIGS. 27 to 29, (a) show the size change in brain tumor and survival rate when the drug is injected by intravenous injection, (b) show a case where the bioelectronic patch device is inserted into the brain tumor region and then only the heating is carried out without the drug injection, (C) shows a case where the bioelectronic patch device is inserted into the brain tumor region and then the drug is released without the heating of the drug patch, and (d) shows a case where the bioelectronic patch device is inserted into the brain tumor region and then the drug is released along with the heating of the drug patch.

Referring to FIGS. 27 and 28, results are as follows. In the case of (a) and (b), the brain tumor rapidly increases with time. In the case of (c), the brain tumor is almost unchanged in the early stage when the size of the brain tumor is small, but the brain tumor slowly increases with time. In the case of (d), as drug release amount and drug penetration depth increase the brain tumor decreases.

Referring to FIG. 29, (c) and (d) show the survival rate higher than (a) and (b). In the case of (d) in particular, the survival rate remains very high even after 50 days elapsed.

As above, the embodiments of the present inventive concept have been disclosed for illustrative purposes. Those skilled in the art will appreciate that the present inventive concept may be embodied in other specific ways without changing the technical spirit or essential features thereof. Therefore, the embodiments disclosed herein are not restrictive but are illustrative. The scope of the present inventive concept is given by the claims, rather than the specification, and also contains all modifications within the meaning and range equivalent to the claims.

INDUSTRIAL APPLICABILITY

A biopatch according to the embodiments of the present inventive concept can be disposed and used in a living body such as a human body. The biopatch can be degraded or absorbed naturally after use. The biopatch can be conformally and strongly adhered to the tissue in the human body such as brain tissue.

A bioheater according to embodiments of the present inventive concept can be disposed and used in a living body such as a human body. The bioheater can be degraded or absorbed naturally after use. The bioheater can be controlled wirelessly and thus is easy to use even if it is disposed in the human body.

A biosensor according to embodiments of the present inventive concept can be disposed and used in a living body such as a human body. The biosensor can be degraded or absorbed naturally after use. The biosensor can be controlled wirelessly and thus is easy to use even if it is disposed in the human body.

A bioelectronic patch device according to embodiments of the present inventive concept can be disposed and used in a living body such as a human body. The bioelectronic patch device can be degraded or absorbed naturally after use. The bioelectronic patch device can be conformally and strongly adhered to the tissue in the human body such as brain tissue. The bioelectronic patch device can effectively deliver the drug to the target position. The bioelectronic patch device can have an excellent effect on the treatment of brain tumors.

The invention claimed is:

1. A biopatch comprising:
   a polymer film comprising a biopolymer;
   a drug loaded in the polymer film; and
   a heater adjacent to the polymer film to heat the polymer film,
   wherein the biopolymer comprises oxidized starch,
   wherein the drug comprises a first drug chemically combined with the oxidized starch and a second drug physically combined with the oxidized starch, and
   wherein the heater comprises a metal pattern formed of biometal and the metal pattern has a plurality of holes.

2. The biopatch of claim 1, wherein an amount of the first drug is controlled by controlling an oxidation concentration of the oxidized starch.

3. The biopatch of claim 1, wherein the biometal comprises Mg or Fe.

4. The biopatch of claim 1, wherein the heater is controlled wirelessly by an alternating magnetic field.

5. The biopatch of claim 1, wherein release of the drug is controlled by the heater.

6. A biopatch comprising:
a polymer film comprising a biopolymer;
a drug loaded in the polymer film;
a heater adjacent to the polymer film to heat the polymer film; and
a temperature sensor adjacent to the heater to measure temperature of the heater,
wherein the biopolymer comprises oxidized starch, and
wherein the drug comprises a first drug chemically combined with the oxidized starch and a second drug physically combined with the oxidized starch.

7. The biopatch of claim 6, wherein the temperature sensor comprises an inductor and a capacitor connected to the inductor, and the capacitor comprises a first electrode, a second electrode facing the first electrode and a dielectric disposed between the first electrode and the second electrode.

8. The biopatch of claim 7, wherein each of the inductor, the first electrode and the second electrode comprises biometal, and the dielectric comprises a biopolymer having a glass transition temperature in a range of 36~42° C.

9. The biopatch of claim 8, wherein the biometal comprises Mg or Fe, and the biopolymer comprises PLGA.

10. The biopatch of claim 7, wherein a dielectric constant of the dielectric changes by a temperature change of the heater, the change in the dielectric constant is transmitted to an external device through a resonance frequency change with the inductor, and the external device measures temperature of the heater by measuring the resonance frequency change wirelessly.

11. The biopatch of claim 1, wherein the biopatch is inserted into brain tissue to be used for treatment of a brain tumor.

12. A bioelectronic patch device comprising:
a drug patch comprising a polymer film comprising a biopolymer and a drug loaded in the polymer film;
a heater adjacent to the drug patch to heat the drug patch; and
a temperature sensor adjacent to the heater to measure temperature of the heater;
wherein the biopolymer comprises oxidized starch, and
wherein the drug comprises a first drug chemically combined with the oxidized starch and a second drug physically combined with the oxidized starch.

13. The bioelectronic patch device of claim 12, wherein an amount of the first drug is controlled by controlling an oxidation concentration of the oxidized starch.

\* \* \* \* \*